United States Patent
Regnier

(10) Patent No.: US 6,872,575 B2
(45) Date of Patent: Mar. 29, 2005

(54) AFFINITY SELECTED SIGNATURE PEPTIDES FOR PROTEIN IDENTIFICATION AND QUANTIFICATION

(75) Inventor: Fred B. Regnier, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 10/244,784

(22) Filed: Sep. 16, 2002

(65) Prior Publication Data

US 2003/0092076 A1 May 15, 2003

Related U.S. Application Data

(62) Division of application No. 09/849,924, filed on May 4, 2001.
(60) Provisional application No. 60/208,184, filed on May 31, 2000, provisional application No. 60/208,372, filed on May 31, 2000, and provisional application No. 60/203,227, filed on May 5, 2000.

(51) Int. Cl.[7] ............... G01N 24/00; G01N 1/00; C08H 1/00
(52) U.S. Cl. ............ 436/174; 436/86; 436/149; 436/173; 530/402
(58) Field of Search ............ 436/86, 89, 106, 436/149, 173, 174; 530/402, 412

(56) References Cited

U.S. PATENT DOCUMENTS

| | | |
|---|---|---|
| 5,393,669 A | 2/1995 | Brown |
| 6,096,717 A | 8/2000 | Jarvik |
| 6,391,649 B1 * | 5/2002 | Chait et al. ......... 436/173 |
| 2002/0076739 A1 | 3/2002 | Aebersold et al. |
| 2002/0119490 A1 | 8/2002 | Aebersold et al. |
| 2003/0087322 A9 | 5/2003 | Aebersold et al. |
| 2003/0129769 A1 | 7/2003 | Regnier |

FOREIGN PATENT DOCUMENTS

| | | |
|---|---|---|
| WO | WO 00/09654 | 2/2000 |
| WO | WO 00/11208 | 3/2000 |
| WO | WO 01/86306 A2 | 11/2001 |

OTHER PUBLICATIONS

Gygi et al., Quantitative Analysis of complex Protein Mixtures Using Isotope–coded Affinity Tags, Oct. 1999, Nature Biotech., 17:994–999.*

Geng et al., Signature–peptide Approach to Detecting Proteins in Complex Mixtures, Feb. 2000, Journal of Chromatography A, 870:295–313.*

Amini et al., "The impact of buffers and surfactants from micellar electrokinetic chromatography on matrix–assisted laser desorption ionization (MALDI) mass spectrometry of peptides. Effect of buffer type and concentration on mass determination by MALDI–time–of–flight mass spectrometry," *Journal of Chromatography A*, 894(1–2):345–355 (2000).

(Continued)

Primary Examiner—Padmashri Ponnaluri
Assistant Examiner—My-Chau T. Tran
(74) Attorney, Agent, or Firm—Mueting, Raasch & Gebhardt, P.A.

(57) ABSTRACT

A method for protein identification in complex mixtures that utilizes affinity selection of constituent proteolytic peptide fragments unique to a protein analyte. These "signature peptides" function as analytical surrogates. Mass spectrometric analysis of the proteolyzed mixture permits identification of a protein in a complex sample without purifying the protein or obtaining its composite peptide signature.

24 Claims, 12 Drawing Sheets

OTHER PUBLICATIONS

Andersen et al., "Functional genomics by mass spectrometry," *FEBS Letters,* 480:25–31 (2000).

Anderson et al., "Twenty years of two–dimensional electrophoresis: past, present and future," *Electrophoresis,* 17(3):443–453 (1996).

Baj et al., "High performance hydrophobic interaction chromatography—A new approach to separate intermediates of protein folding." *Chinese Chemical Letters* 8(1):67–70 (1997).

Clauser et al., "Rapid mass spectrometric peptide sequencing and mass matching for characterization of human melanoma proteins isolated by two–dimensional PAGE," *Proceedings of the National Academy of Sciences USA,* 92(11):5072–5076 (1995).

Corthals et al., "Chapter 10: Identification of Proteins by Mass Spectrometry," *Proteome Research: Two–Dimensional Gel Electrophoresis and Identification Methods,* Rabilloud, ed., Springer Verlag, Heidelberg, Germany, title page, publication page, and pp. 197–231 (2000).

Corthals et al., "Identification of proteins by mass spectrometry," *Proteome Research: Two–Dimensional Gel Electrophoresis and Identification Methods,* selected portion available on–line, The Garvan Institute of Medical Research, Biological Mass Spectrometry and Protein Analysis Laboratory [on–line] New York, NY, Springer, 1999 [retrieved on Sep. 12, 2001]. Retrieved from the Internet: <URL: http://www.garvan.unsw.edu.au/public/corthals/book/IPMS.html>, pp. 1–17.

Dormady, Shelly J., "Novel Applications of Bioanalytical Techniques for Proteomic Research," Ph.D. Thesis, Purdue University, (cover date May 2000).

Dormady et al., "Eliminating disulfide exchange during glutamyl endopeptidase digestion of native protein," *Journal of Chromatography A,* 864:237–245 (1999).

Dunlap et al., "Synthesis and chromatographic characterization of dextran–coated zirconia high–performance liquid chromatographic stationary phases," *Journal of Chromatography A,* 746(2):199–210 (1996).

Eng et al., "An Approach to Correlate Tandem Mass Spectral Data of Peptides with Amino Acid Sequences in a Protein Database," *Journal of the American Society for Mass Spectrometry,* 5(11):976–989 (1994).

Geng, Ming Hui "The Proteomics of Glycoproteins," Ph.D. Thesis, Purdue University (cover date Aug. 2000).

Geng et al., "Proteomics of Glycoproteins Based on Affinity Selection of Glycopeptides from Tryptic Digest," *Journal of Chromatography B,* 752:293–306 (2001).

Goodlett et al., "Protein Identification with a Single Accurate Mass of a Cysteine–Containing Peptide and Constrained Database Searching," *Analytical Chemistry,* 72(6):1112–1118 (2000).

Gygi et al., "Measuring gene expression by quantitative proteome analysis," *Current Opinion in Biotechnology,* 11(4):396–401 (2000).

Gygi et al., "Mass spectrometry and proteomics," *Current Opinion in Chemical Biology,* 4(5):489–494 (2000).

Hunter et al. "Novel receptor protein–tyrosine kinases" *Adv Second Messenger Phosphoprotein Res.* 1990;24:260–5.

Hsieh et al., "Separation and Identification of Peptides in Single Neurons by Microcolumn Liquid Chromatography–Matrix–Assisted Laser Desorption/Ionization Time–of–Flight Mass Spectrometry and Postsource Decay Analysis," *Analytical Chemistry,* 70(9):1847–1852 (1998).

Hsieh et al., "Automated Analytical System for the Examination of Protein Primary Structure," *Analytical Chemistry,* 68:455–462 (1996).

Ji et al., "Strategy for qualitative and quantitative analysis in proteomics based on signature peptides," *Journal of Chromatography B,* 745:197–210 (2000).

Kosaka et al., "Identification and C–Terminal Characterization of Proteins from Two–Dimensional Polyacrylamide Gels by a Combination of Isotopic Labeling and Nanoelectrospray Fourier Transform Ion Cyclotron Resonance Mass Spectrometry," *Analytical Chemistry,* 72:1179–1185 (2000).

Lee et al., "Enzymatic and Chemical Digestion of Proteins for Mass Spectrometry," *Methods in Enzymology,* 193:361–374 (1990).

Link et al., "Direct analysis of protein complexes using mass spectrometry," *Nature Biotechnology,* 17(10):676–682 (1999).

Nelson et al., "BIA/MS of Epitope–Tagged Peptides Directly from *E. coli* Lysate: Multiplex Detection and Protein Identification at Low–Femtomole to Subfemtomole Levels," *Analytical Chemistry,* 71:2858–2865 (1999).

O'Farrell, "High Resolution Two–Dimensional Electrophoresis of Proteins," *The Journal of Biological Chemistry,* 250(10):4007–4021 (1975).

Patterson et al., "C–Terminal Ladder Sequencing via Matrix–Assisted Laser Desorption Mass Spectrometry Coupled with Carboxypeptidase Y Time–Dependent and Concentration–Dependent Digestions," *Analytical Chemistry,* 67(21):3971–3978 (1995).

Pedersen et al., "Patterns of Protein Synthesis in *E. coli*: a Catalog of the Amount of 140 Individial Proteins at Different Growth Rates," *Cell,* 14(1):179–190 (1978).

Perkin–Elmer Applied Biosystems Press Release, "PE Biosystems Obtains Exclusive License for ICAT™ Reagents for Proteomics," [online]. Applied Biosytsems, Foster City, Calif., Nov. 17, 2000 [retrieved on Sep. 26, 2001]. Retrieved from the Internet: <URL:www.appliedbiosystems.com/press_release/icat> 2 pages.

Poehlein, Sara Kim, "I. Applications of fourier transform ion–cyclotron–resonance mass spectrometry to the studies of the isomers of the organometallic distronic ion and the reactivity of cobalt iodide. II. Analysis of polymers by matrix–assisted laser desorption ionization TOF," Ph.D. Thesis, Purdue University, 152 pages (cover date Aug. 1999).

Porath, "Immobilized Metal Ion Affinity Chromatography," *Protein Expression and Purification,* 3(4):263–281 (1992).

Porath et al., "Metal chelate affinity chromatography, a new approach to protein fractionation," *Nature,* 258(5536):598–599 (1975).

Posewitz et al., "Immobilized Gallium(III) Affinity Chromatography of Phosphopeptides," *Analytical Chemistry,* 71(14):2883–2892 (1999).

Raj et al., "Indoles and auxins. X. 2,4–Dinitrophenylsulfenyl chloride, a reagent for separation and identification of naturally–occurring indoles," *Canadian Journal of Biochemistry,* 48(6):664–670 (1970).

Raj et al., "Indoles and auxins. V. Separation of 2,4–dinitrophenylthio–derivatives of naturally occurring indoles by thin layer chromatography," *Journal of Chromatography,* 44(1):199–201 (1969).

Regnier, Fred E., "Chip Based Systems for the Analysis of Regulation," Grant Abstract, Grant No. 1R01GM059996–01 [online]. National Institutes of General Medical Sciences, National Institutes of Health, project dates Sep. 01, 1999–Aug. 31, 2003 [retrieved on Sep. 10, 2001].

Regnier, Fred E., "Chip Based Systems for the Analysis of Regulation," Grant Abstract, Grant No. 5R01GM059996–02 [online]. National Institutes of General Medical Sciences, National Institutes of Health, project dates Sep. 01, 1999–Aug. 31, 2003 [retrieved on Aug. 10, 2001].

Regnier et al., "Chromatography and electrophoresis on chips: critical elements of future integrated, microfluidic analytical systems for life science," *Trends in Biotechnology*, 17(3):101–106 (1999).

Regnier, Fred E., "High Speed Liquid Chromatography of," Grant Abstract, Grant No. 1R01GM025431–01 [online]. National Institutes of General Medical Sciences, National Institutes of Health, project dates Jul. 01, 1978–Jun. 30, 1980 [retreived on Sep. 10, 2001].

Regnier, Fred E., "High Speed Liquid Chromatography of," Grant Abstract, Grant No. 5R01GM025431–02 [online]. National Institutes of General Medical Sciences, National Institutes of Health, project dates Jul. 01, 1978–Jun. 30, 1980 [retrieved on Sep. 10, 2001].

Regnier, Fred E., "High Performance Liquid Chromatography of Proteins," Grant Abstract, Grant No. 2R01GM025431–03 [online]. National Institutes of General Medical Sciences, National Institutes of Health, project dates Jul. 01, 1978–Jun. 30, 1983 [retrieved on Sep. 10, 2001].

Regnier, Fred E., "High Performaince Liquid Chromatography of Proteins," Grant Abstract, Grant No. 5R01GM025431–04 [online]. National Institutes of General Medical Sciences, National Institutes of Health, project dates Jul. 01, 1978–Jun. 30, 1983 [retrieved on Sep. 10, 2001].

Regnier, Fred E., "High Performance Liquid Chromatography of Proteins," Grant Abstract, Grant No. 5R01GM025431–05 [online], National Institutes of General Medical Sciences, National Institutes of Health, project dates Jun. 01, 1978–Jun. 30, 1983 [retrieved on Sep. 10, 2001].

Regnier, Fred E., "High Performance Liquid Chromatography of Proteins," Grant Abstract, Grant No. 2R01GM025431–06 [online]. National Institutes of General Medical Sciences, National Institutes of Health, project dates Jul. 01, 1978–Jun. 30, 1988 [retrieved on Sep. 10, 2001].

Regnier, Fred E., "High Performance Liquid Chromatography of Proteins," Grant Abstract, Grant No. 5R01GM025431–07 [online]. National Institutes of General Medical Sciences, National Institutes of Health, project dates Jul. 01, 1978–Jun. 30, 1988 [retrieved on Sep. 10, 2001].

Regnier, Fred E., "High Performance Liquid Chromatography of Proteins," Grant Abstract, Grant No. 5R01GM025431–08 [online]. National Institutes of General Medical Sciences, National Institutes of Health, project dates Jul. 01, 1978–Jun. 30, 1988 [retrieved on Sep. 10, 2001].

Regnier, Fred E., "High Performmance Liquid Chromatography of Proteins," Grant Abstract, Grant No. 5R01GM025431–09 [online]. National Institutes of General Medical Sciences, National Institutes of Health, project dates Jul. 01, 1978–Jun. 30, 1988 [retrieved on Sep. 10, 2001].

Regnier, Fred E., "High Performance Liquid Chromatography of Proteins," Grant Abstract, Grant No. 5R01GM025431–01 [online]. National Institutes of General Medical Sciences, National Institutes of Health, project dates Jul. 01, 1978–Jun. 30, 1988 [retrieved on Sep. 10, 2001].

Regnier, Fred E., "High Performance Liquid Chromatography of Proteins," Grant Abstract, Grant No. 2R01GM025431–11 [online]. National Institutes of General Medical Sciences, National Institutes of Health, project dates Jul. 01, 1978–Jun. 30, 1993 [retrieved on Sep. 10, 2001].

Regnier, Fred E., "High Performance Liquid Chromatography of Proteins," Grant Abstract, Grant No. 5R01GM025431–12 [online]. National Institutes of General Medical Sciences, National Institutes of Health, project dates Jul. 01, 1978–Jun. 30, 1993 [retrieved on Sep. 10, 2001].

Regnier, Fred E., "High Performance Liquid Chromatography of Proteins," Grant Abstract, Grant No. 5R01GM02543–13 [online]. National Institutes of General Medical Sciences, National Institutes of Health, project dates Jul. 01, 1978–Jun. 30, 1993 [retrieved on Sep. 10, 2001].

Regnier, Fred E., "High Performance Liquid Chromatography of Proteins," Grant Abstract, Grant No. 5R01GM025431–14 [online]. National Institutes of General Medical Sciences, National Institutes of Health, project dates Jul. 01, 1978–Jun. 30, 1993 [retrieved on Sep. 10, 2001].

Regnier, Fred E., "High Performance Liquid Chromatography of Proteins," Grant Abstract, Grant No. 5R01GM025431–15 [online]. National Institutes of General Medical Sciences, National Institutes of Health, project dates Jul. 01, 1978–Mar. 31, 1994 [retrieved on Sep. 10, 2001].

Regnier, Fred E., "Molecularly Imaged Media for HPLC of Proteins," Grant Abstract, Grant No. 2R01GM025431–16A1 [online]. National Institutes of General Medical Sciences, National Institutes of Health, project dates Jul. 01, 1978–Mar. 31, 1998 [retrieved on Sep. 10, 2001].

Regnier, Fred E., "Molecularly Imaged Media for HPLC of Proteins," Grant Abstract, Grant No. 5R01GM025431–17 [online]. National Institutes of General Medical Sciences, National Institutes of Health, project dates Jul. 01, 1978–Mar. 31, 1998 [retrieved on Sep. 10, 2001].

Regnier, Fred E., "Molecularly Imaged Media for HPLC of Proteins," Grant Abstract, Grant No. 5R01GM025431–18 [online]. National Institutes of General Medical Sciences, National Institutes of Health, project dates Jul. 01, 1978–Mar. 31, 1998 [retrieved on Sep. 10, 2001].

Regnier, Fred E., "Molecularly Imaged Media for HPLC of Proteins," Grant Abstract, Grant No. 5R01GM025431–19 [online]. National Institutes of General Medical Sciences, National Institutes of Health, project dates Jul. 01, 1978–Mar. 31, 1999 [retrieved on Sep. 10, 2001].

Regnier et al., "Multidimensional Chromatography and the Signature Peptide Approach to Proteomics," *LCGC, 19*(2):201–213, (Feb. 2001).

Regnier et al., "Multidimensional Chromatography and the Signature Peptide Approach to Proteomics," *LCGC, 19*(2) Feb. 2001 [online], [retrieved on Sep. 10, 2001].

Reiber et al., "Identifying Proteins Using Matrix–Assisted Laser Desorption/Ionization In–Source Fragmentation Data Combined with Database Searching," *Analytical Chemistry, 70*(3):673–683 (1998).

Riggs et al., "Automated signature peptide approach for proteomics," *Journal of Chromatography A, 924*(1–2):359–368 (Jul. 27, 2001).

Roquemore et al., "Detection of O–linked N–Acetylglucosamine (O–GlcNAc) on Cytoplasmic and Nuclear Proteins," *Methods in Enzymology, 230*:443–460 (1994).

Schena et al., "Quantitative Monitoring of Gene Expression Patterns with a Complementary DNA Microarray," *Science, 270*, 467–470 (1995).

Schena et al., "Parallel human genome analysis: Microarray–based expression monitoring of 1000 genes," *Proceedings of the National Academy of Sciences USA, 93*(20):10614–10619 (1996).

Scoffone et al., "Sulfenyl Halides as Modifying Reagents for Polypeptides and Proteins. I. Modification of Tryptophan Residues," *Biochemistry, 7*(3):971–979 (1968).

VanBogelen et al., "Gene–Protein Database of *Escherichia coli* K–12, Edition 6," in *Escherichia Coli and Salmonella, Cellular and Molecular Biology, 2nd Ed., vol. 2*, Neidhardt et al., eds., ASM Press, Washington, D.C., Title page, publication p. and pp. 2067–2117 (1996).

Wang et al., "Proteomics based on selecting and quantifying cysteine containing peptides by covalent chromatography," *Journal of Chromatography A, 924*(1–2):345–357 (Jul. 27, 2001).

Wilchek, "Isolation of Specific and Modified Peptides Derived from Proteins," *Methods of Enzymology, 34*:182–195 (1974).

Wilcheck et al., "The isolation of tryptophan–containing peptides by affinity chromatography," *Biochimicia et Biophysica Acta, 278*(1):1–7 (1972).

Yates, III, et al., "Direct Analysis of Protein Mixtures by Tandem Mass Spectrometry," *Journal of Protein Chemistry, 16*(5):495–497 (1997).

Yates, III, "Mass Spectrometry and the Age of the Proteome," *Journal of Mass Spectrometry, 33*(1):1–19 (1998).

Zhang et al., "Analysis of channel–geometry effects on separation efficiency in rectangular–capillary electrochromatography columns," *Journal of Chromatography A, 869*(1–2):319–328 (2000).

Zhang, Xiang, "Informatics of Signature Peptide Approach to Proteomics," Ph.D. Thesis, Purdue University, (cover date Dec. 2001).

Zhang et al., "Capillary Electrophoresis Combined with Matrix–Assisted Laser Desorption/Ionization Mass Spectrometry; Continuous Sample Deposition on a Matrix–precoated Membrane Target," *Journal of Mass Spectrometry, 31*(9):1039–1046 (1996).

\* cited by examiner

Fig. 1

AFFINITY SELECTED SIGNATURE PEPTIDES FOR PROTEIN IDENTIFICATION AND QUANTIFICATION

This is a division of application Ser. No. 09/849,924, filed May 4, 2001, (pending), which claims the benefit of application Ser. No. 60/203,227, filed May 5, 2000, Ser. No. 60/208,372, filed May 31, 2000, and Ser. No. 60/208,184, filed May 31, 2000, which are incorporated herein by reference.

STATEMENT OF GOVERNMENT RIGHTS

This invention was made with government support under a grant from the National Institutes of Health, Grant Nos. 25431 and GM 59996. The U.S. Government has certain rights in this invention.

BACKGROUND OF THE INVENTION

DNA sequencing of the human genome has profoundly advanced our understanding of the molecular anatomy of mammalian cells. However, knowing the sequence of all the genes in a cell and extrapolating from this the probable products a cell is capable of producing is not enough. It is clear that i) not all genes are expressed to the same degree; ii) the DNA sequence does not always tell you the structure of a protein in the cases of post-transcriptional and post-translational modifications; iii) knowing the sequence of a gene tells you nothing about the control of expression; iv) control of genetic expression is extremely complicated and can vary from protein to protein; v) post-translational modification can occur without de novo protein biosynthesis; and vi) variables other than genomic DNA can be responsible for disease.

In addition, it has recently become apparent that there is a poor correlation between genetic expression of mRNA, generally measured as cDNA, and the amount of protein expressed by that mRNA. Changes in mRNA concentration are not necessarily proportional to changes in protein concentration. There are even many cases where mRNA will be up regulated and protein concentration will not change at all. The steady state concentration of a protein can depend on the relative degree of expression from multiple genes and the activity of these gene products in the synthesis of a specific protein. Glycoproteins provide a good example. The concentration of a glycoprotein can depend on the level to which the gene coding for the polypeptide backbone is regulated, the presence of all the enzymes responsible for the synthesis and attachment of the oligosaccharide to the polypeptide, and the concentration of glycosidases and proteases that degrade the glycoprotein. For these reasons, analysis of regulation using messenger RNA-based techniques such as "DNA chips" alone is inadequate. It is clear that measuring the concentration of mRNA that codes for the polypeptide backbone may either distort or fail to recognize the total picture of how a protein is regulated. In cases where it is desirable to know how protein expression levels change, direct measurement of those levels may be needed.

Concentration and expression levels of specific proteins vary widely in cells during the life cycle, both in absolute concentration and amount relative to other proteins. Over- or under-expression are known to be indicators of genetic errors, faulty regulation, disease, or a response to drugs. However, the small number of proteins that are up- or down-regulated in response to a particular stimulus are difficult to recognize with current technology. Further, it is frequently difficult to predict which proteins are subject to regulation. The need to examine 20,000 proteins in a cell to find the small number in regulator flux is a formidable problem. The ability to detect only the small numbers of up- or down-regulated proteins in a complex protein milieu would substantially enhance the value of proteomics.

Proteins in complex mixtures are generally detected by some type of fractionation or immunological assay technique. The advantages of immunological assay methods are their sensitivity, specificity for certain structural features of antigens, low cost, and simplicity of execution. Immunological assays are generally restricted to the determination of single protein analytes. This means it is necessary to conduct multiple assays when it is necessary to determine small numbers of proteins in a sample. Hormone-receptor association, enzyme-inhibitor binding, DNA-protein binding and lectin-glycoprotein association are other types of bioaffinity that have been exploited in protein identification, but are not as widely used as immunorecognition. Although not biospecific, immobilized metal affinity chromatography (IMAC) is yet another affinity method that recognizes a specific structural element of polypeptides (J. Porath et al., *Nature* 258: 598–599 (1992)).

The fractionation approach to protein identification in mixtures is often more lengthy because analytes must be purified sufficiently to allow a detector to recognize specific features of the protein. Properties ranging from chemical reactivity to spectral characteristics and molecular mass have been exploited for detection. Higher degrees of purification are required to eliminate interfering substances as the detection mode becomes less specific. Since no single purification mode can resolve thousands of proteins, multi-dimensional fractionation procedures must be used with complex mixtures. Ideally, the various separation modes constituting the multidimensional method should be orthogonal in selectivity. The two-dimensional (2D) gel electrophoresis method of O'Farrel (*J. Biol. Chem.* 250:4007–4021 (1975)) is a good example. The first dimension exploits isoelectric focusing while the second is based on molecular size discrimination. At the limit, 6000 or more proteins can be resolved. 2D gel electrophoresis is now widely used in proteomics where it is the objective to identify thousands of proteins in complex biological extracts.

The most definitive way to identify proteins in gels is by mass spectral analysis of peptides obtained from a tryptic digest of the excised spot. Digestion of an excised spot with trypsin typically generates about 30–200 peptides. Identification is greatly facilitated when peptide molecular mass can be correlated with tryptic cleavage fragments predicted from a genomic database. Computer-assisted mathematical deconvolution algorithms are used to identify a protein based upon its "composite peptide signature." Proteins can also be identified by their separation characteristics alone in some cases. The advantage of 2D electrophoresis followed by tryptic mapping is that large numbers of proteins can be identified simultaneously. However, the disadvantages of the technique are (1) it is very slow and requires a large number of either manual or robotic manipulations, (2) charged isoforms are resolved whereas uncharged variants in which no new charge is introduced are not, (3) proteins must be soluble to be examined, and (4) quantification by staining is poor.

In addition to being used to identify proteins, 2-D gel electrophoresis has also been used to assess relative changes in protein levels. The degree to which the concentration of a protein changes can be determined by staining the gel and visually observing those spots that changed. Alternatively, changes in the concentration of a protein can be quantitated with a gel scanner. A control 2-D gel is required to determine the concentration of the protein before it was either up or down regulated. Tryptic cleavage of the excised spot and mass analysis using mass spectrometry remains necessary to identify the protein whose expression level has changed.

Promising new techniques are emerging that replace 2-D gel electrophoresis. Most involve some combination of high performance liquid chromatography (HPLC) or capillary electrophoresis (CE) with mass spectrometry to either create a "virtual 2-D gel" or go directly to the peptide level of analysis by tryptic digesting all the proteins in samples as the initial step of analysis. The use of multidimensional chromatography (MDC) to identify proteins in a complex mixture is faster, easier to automate, and couples more readily to MS than 2D gel electrophoresis. One of the more attractive features of chromatographic systems is that they allow many dimensions of analysis to be coupled by analyte transfer between dimensions through automated valve switching. A recent report of an integrated six dimensional analytical system in which serum hemoglobin was purified and sequenced automatically in <2 hours is an example (F. Hsieh et al., *Anal. Chem.* 68:455 (1996)). Subsequent to purification on an immunoaffinity column, hemoglobin was desorbed into an ion-exchange column for buffer exchange and then tryptic digested by passage through an immobilized trypsin column. Peptides eluting from the immobilized enzyme column were concentrated and desalted on a small, low-surface-area reversed-phase liquid chromatography (RPLC) column and then transferred to an analytical RPLC column where they were separated and introduced into a mass spectrometer through an electrospray interface. Identification at the primary structure level was achieved by a combination of chromatographic properties and multidimensional mass spectrometry of the tryptic peptides. The ability of the immunosorbant to rapidly select the desired analyte for analysis was a great asset to this analysis. Size-exclusion or ion-exchange chromatography coupled to reversed-phase chromatography are other examples of multidimensional systems, albeit of lower selectivity than those using immunosorbant.

Although the methods described above are highly selective and widely used, they have some attributes that limit their efficacy. One is the need for proteins to be soluble before than can be analyzed. This can be a serious limitation in the case of membrane and structural proteins that are sparingly soluble. A second is that it is desirable or even necessary in some cases for the protein analyte to be of native structure during at least part of the analysis. This is a limitation because it restricts the sample preparation protocol. Native macromolecular structures are notoriously more difficult to analyze than small molecules. The necessity for post separation proteolysis, as in the 2D gel approach, is another limitation. Large numbers of fractions must be subjected to a 24 hour tryptic digestion protocol in the analysis of a single sample when many proteins are being identified. The tryptic digestion step is necessary because the mass of intact proteins is far less useful in searching DNA databases than that of peptides derived from the protein. And finally, pure proteins are a prerequisite for antibody preparation in all the immunorecognition methods. The preparation of antibodies to an antigen is lengthy, laborious, and costly, and many antigens have never been purified. This is particularly true of proteins predicted by genomic data alone. Purification is complicated by the fact that one does not know the degree to which a protein is expressed, whether it is part of a multisubunit complex, or if it is post translationally modified.

Additionally, there is the issue of quantification. Measuring either the relative abundance of proteins or changes in protein concentration remains a major challenge in proteomics. Improved methods for protein identification, quantification and detection of regulatory (or relative change) or proteins, especially for the identification and quantification of proteins within a complex mixture, are clearly needed to advance the new science of proteomics.

SUMMARY OF THE INVENTION

The present invention provides a method for protein identification and quantification in complex mixtures that utilizes affinity selection of constituent peptide fragments. These peptides function as analytical surrogates for the proteins. The method of the invention makes it possible to identify a protein in a sample, preferably a complex sample, without sequencing the entire protein. In many cases the method allows for identification of a protein in a sample without sequencing any part of the protein.

To "identify a protein" as that phrase is used herein means to determine the identity of a protein or a class of proteins to which it belongs. Identifying a protein within a complex mixture of proteins involves determining the presence or absence of a particular protein or class of proteins in the mixture. Prior to identifying the protein according to the method of the invention, it may be suspected that a particular protein is in the mixture. On the other hand, the protein content of the mixture may be largely unknown. Protein identification according to the method may be used, for example, to catalog the contents of a complex mixture or to discover heretofore unknown proteins (e.g., proteins that are predicted from the genome but have not yet been isolated).

Proteolysis of most proteins yields at least one unique "signature peptide." The method of the invention identifies these constituent signature peptides, preferably utilizing mass spectrometry, thereby allowing the protein comprising the signature peptide to be distinguished from all other proteins in a complex mixture and identified.

Constituent peptides can provide a generic signature for proteins as well, especially when major portions of the amino acid sequence of a series of protein variants are homologous. Glycoprotein variants that differ in degree of glycosylation but not amino acid sequence are an example. Proteins that have been modified by proteolysis are another case. Peptides that are unique to a variety of species of similar structure are defined as "generic signature peptides", and the invention thus allows identification of a class of proteins by detecting and characterizing their generic signature peptides.

Proteins in a sample are initially fragmented, either as part of the method or in advance of applying the method. Fragmentation in solution can be achieved using any desired method, such as by using chemical, enzymatic, or physical means. It should be understood that as used herein, the terms "cleavage", "proteolytic cleavage", "proteolysis", "fragmentation" and the like are used interchangeably and refer to scission of a chemical bond within peptides or proteins in solution to produce peptide or protein "fragments" or "cleavage fragments." No particular method of bond scission is intended or implied by the use of these terms. Fragmentation and the formation of peptide cleavage fragments in solution are to be differentiated from similar processes in the gas phase within a mass spectrometer. These terms are context specific and relate to whether bond scission is occurring in solution or the gas phase in a mass spectrometer.

Prior to proteolytic cleavage, the proteins are preferably alkylated with an alkylating agent in order to prevent the formation of dimers or other adducts through disulfide/dithiol exchange; optionally, the proteins are reduced prior to alkylation in order to facilitate the alkylation reaction and subsequent fragmentation. Some proteins are resistant to proteolysis unless they have been reduced and alkylated prior to cleavage.

At least one peptide derived from the protein to be identified preferably includes at least one affinity ligand. The affinity ligand can be endogenous or exogenous. Preferably, the affinity ligand is endogeneous, thereby simplifying the method. If exogenous, the method optionally includes covalently attaching at least one affinity ligand to at least one protein (or peptide) in the sample before (or after) proteolytic cleavage. Optionally, the affinity ligand is covalently linked to the alkylating agent. The peptides are then contacted with a capture moiety to select peptides that contain the at least one affinity ligand. If desired, a plurality of affinity ligands are attached, each to at least one protein or peptide, and the peptides are contacted with a plurality of capture moieties to select peptides that contain at least one affinity ligand. Optionally, the selected peptides are fractionated at this point in order to further simplify the mixture and make it amenable to mass spectrometric analysis, yielding a plurality of peptide fractions.

Peptides are analyzed by mass spectrometry to detect at least one peptide derived from the protein to be identified, thereby permitting identification of the protein(s) from which the detected peptide was derived. When the detected peptide is a signature peptide, the method further includes determining the mass of the signature peptide and using the mass of the signature peptide to identify the protein from which the detected peptide was derived. Optionally, the amino acid sequence of all or a portion of a detected peptide can be determined and used to identify the protein from which the detected peptide was derived. In a preferred embodiment, the mass of the signature peptide is compared with the masses of reference peptides derived from putative fragmentation of a plurality of reference proteins in a database, wherein the masses of the reference peptides are adjusted to include the mass of the affinity ligand, if necessary. Prior to making this comparison, reference peptides are optionally computationally selected to exclude those that do not contain an amino acid upon which the affinity selection is based in order to simplify the databases comparison.

The advantages of the method for protein identification of the invention are numerous. Proteins themselves (which are large molecules compared to peptides) do not need to be separated electrophoretically or chromatographically, both time consuming steps. Moreover, affinity selection yields a subpopulation of peptides (typically eliminating about 90% of peptides) that is, advantageously, enriched for "signature peptides." If desired, multiple selections can be used to produce the enriched, affinity-selected population, further simplifying the process of protein identification. In many cases, a protein can be identified from its signature peptides; it is not necessary to purify the protein, sequence any part of it, or determine its composite peptide signature in order to identify it.

The present invention further provides a post-synthetic isotope labeling method useful for detecting differences in the concentration of metabolites between two samples. Application of the isotope labeling method of the invention is not limited to proteins, but can be used to identify or quantitate other metabolites as well such as lipids, nucleic acids, polysaccharides, glycopeptides, glycoproteins, and the like. The samples are preferably complex mixtures, and the metabolite is preferably a protein or a peptide. Advantageously, the method can be utilized with complex mixtures from various biological environments. For example, the method of the invention can be used to detect a protein or family of proteins that are in regulatory flux in response to the application of a stimulus. Peptides derived from these proteins exhibit substantially the same isotope ratios, which differ from the normalized isotope ratio determined for proteins that are not in flux, indicating that they are co-regulated. Or, samples can be obtained from different organisms, cells, organs, tissues or bodily fluids, in which case the method permits determination of the differences in concentration of at least one protein in the organisms, cells, organs, tissues or bodily fluids from which the samples were obtained.

The post-synthetic isotope labeling method of the invention involves attaching a first chemical moiety to a protein, peptide, or the cleavage products of a protein in a first sample and a second chemical moiety to a protein, peptide, or the cleavage products of a protein in a second sample to yield first and second isotopically labeled proteins, peptides or protein cleavage products, respectively, that are chemically equivalent yet isotopically distinct. The chemical moiety can be a single atom (e.g., oxygen) or a group of atoms (e.g., an acetyl group). The labeled proteins, peptides or peptide cleavage products are isotopically distinct because they contain different isotopic variants of the same chemical entity (e.g, a peptide in the first sample contains $^1H$ where the peptide in the second sample contains $^2H$; or a peptide in the first sample contains $^{12}C$ where the peptide in the second sample contains $^{13}C$).

When a complex protein mixture is being analyzed, isotopic labeling can be performed either before or after cleavage of the proteins. Preferably, isotopic labeling is performed after cleavage, and the first and second chemical moieties are attached to at least one amino group, preferably the N-terminus, and/or at least one carboxylic acid group, preferably the C-terminus, on the peptides. Conveniently, the N-termini of proteins or peptides can be labeled in an acetylation reaction, and/or the C-termini of proteins or peptides can be labeled by incorporation of $^{18}O$ from $H_2{}^{18}O$ in the hydrolysis reaction. In the latter case, one chemical moiety is represented by $^{16}O$, the naturally occurring isotope, and the other chemical moiety is represented by $^{18}O$; in effect, this particular process can be considered as "isotopically labeling" only one of the samples (the one that carries the $^{18}O$ isotope). When both the N-termini and the C-termini of proteins or peptides are isotopically labeled, it is possible to differentiate between C-terminal peptides, N-terminal blocked peptides, and those that are internal. Labeling both the N- and C-terminus of the proteins or peptides also facilitates the analysis of single amino acid polymorphisms. Labeling at the N- and/or C-terminus allows all or substantially all proteolytic peptides to be labeled, the advantages of which are discussed below.

At least a portion of each sample is typically mixed together to yield a combined sample, which is subjected to mass spectrometric analysis. Control and experimental samples are mixed after labeling, fractions containing the desired components are selected from the mixture, and concentration ratio is determined to identify analytes that have changed in concentration between the two samples. However, actual mixing of the samples is not required, and the mass spectrometric analysis can be carried out on each sample independently, then analyzed with the assistance of a computer to achieve the same end. This important feature of the method significantly reduces processing time and facilitates automation of the process.

The members of at least one pair of chemically equivalent, isotopically distinct peptides optionally include at least one affinity ligand. The affinity ligand can be endogenous or exogenous. If exogenous, the method optionally includes covalently attaching at least one affinity ligand to at least one protein (or peptide) in the sample before (or after) proteolytic cleavage. Optionally, the affinity ligand is covalently linked to the alkylating agent. Prior to determining the isotope ratios, the peptides are contacted with a capture moiety to select peptides which contain the at least one affinity ligand. If desired, a plurality of affinity ligands can be attached, each to at least one protein or peptide, and the peptides are contacted with a plurality of capture moieties to select peptides that contain at least one affinity ligand. In a preferred embodiment, at least one "signature peptide" unique to a protein is selected, and the signature peptide is subsequently used to identify the protein from which it was derived.

In a preferred embodiment, the affinity ligand is distinct from the isotope labeling moieties. In other words, the labeling step is not coupled to the selection step. This allows the quantitation function and the selection function to be independent of one another, permitting more freedom in the choice of reagents and labeling sites and also allowing an isotopically labeled sample to be assayed for different signature peptides. Another advantage of uncoupling the labeling and selection steps is that labeling, if performed after cleavage, can be applied in a manner to label all peptides, not just the peptide to be selected.

When the method involves labeling all peptide fragments, it is referred to herein as the global internal standard technology (GIST) method (FIG. 1). Components from control samples function as standards against which the concentration of components in experimental samples are compared. When the differential labeling process is directed at primary amine, carboxyl groups, or both in peptides produced during proteolysis of the proteome, an internal standard is created for essentially every peptide in the mixture. Possible, but rare, exceptions to this include peptides that are derivatized or blocked on the N-terminus or C-terminus. Examples of N-terminal blocking include f-met proteins found in bacterial systems, acylation of serum proteins, and the formation of the cyclic moiety pyrrolidone carboxylic acid (pyroGlu or pGlu) at an N-terminal glutamate. The C-terminus can be blocked due to the formation of an amide or an ester; for example many prenylated proteins are blocked at the C-terminus with a methyl ester. In any event, because virtually all peptide fragments in the sample are labeled, the method is referred to as a global labeling strategy. This global internal standard technology (GIST) for labeling may be used to quantifying the relative concentration of all components in complex mixtures.

As an example, an investigator can isotopically label all peptides (by labeling the free amino group or the free carboxyl group that characterizes nearly every peptide), then independently affinity label the isotopically labeled peptides at other sites, either in parallel or in series. Perhaps tyrosines in an aliquot of a globally isotopically labeled peptide pool could be affinity labeled (either before or after protein fragmentation), after which peptides containing tyrosines could be selected. Then, another aliquot of the same peptide pool could be selected for histidine-containing peptides. Alternatively, the selected tyrosine-containing peptide subpopulation could be further selected for histidine, depending on the interests of the investigator. Isotope ratios for any of these selected peptides could be determined using mass spectrometry. See Example V for examples of multiple selections on globally isotopically labeled peptides.

Although the advantages of keeping the isotopic labeling step independent of the selection criteria are significant and very clear, it should nonetheless be understood that, if desired, the affinity ligand and the first and second moieties used to isotopically label the peptides or proteins can be the same, as in the case where proteins or peptide are affinity labeled at cysteine with isotopically distinct forms of the alkylating agent, iodoacetic acid, coupled to the affinity ligand biotin. It is significant that if cysteine-containing peptides are to be selected, the investigator is generally limited to derivatizing the protein prior to cleavage, as part of the reduction and alkylation process. In addition, it should be cautioned that whenever isotopically labeling is coupled to the selection process, only a subpopulation of the peptide fragments will be isotopically labeled. Moreover, only one selection criterion can be effectively used for comparative quantitative analysis of peptides. Application of a second selection criterion selects for peptides that are not necessarily isotopically labeled, rendering quantitative comparison impossible. If a second selection is desired, the protein or peptide sample must be isotopically labeled a second time with the new derivatizing agent.

Furthermore, unless peptides are globally labeled isotopically, it is not possible to select and quantitatively compare peptides on the basis of an inherent feature of the peptide (i.e., an endogenous affinity ligand). For example, tyrosinephosphate-containing peptides selected using immunochromatrography, or histidine-containing peptides selected using IMAC (see below) could not be quantitatively compared unless a global isotopic labeling strategy was used. Selection using an endogenous affinity ligand (as opposed to an exogenous ligand that needs to be linked to the peptide in a separate step) is preferred in the method of the invention, therefore the ability to globally label the peptides is an extremely important and useful aspect of the invention.

Optionally in the method of the invention, at some point prior to determining the isotope ratios, the combined peptide sample is fractionated, for example using a chromatographic or electrophoretic technique, to reduce its complexity so that it is amenable to mass spectrometric analysis, yielding at least one fraction containing the isotopically labeled first and second proteins and/or peptides.

During mass spectrometric analysis, a normalized isotope ratio characterizing metabolites whose concentration is the same in the first and second samples is first determined, then the isotope ratio of the first and second isotopically labeled metabolites is determined and compared to the normalized isotope ratio. A difference in the isotope ratio of the first and second isotopically labeled metabolites and the normalized isotope ratio is indicative of a difference in concentration of the metabolite in the first and second samples.

When the metabolites are affinity-labeled peptides derived from a protein, mass spectrometric analysis can be used to detect at least one peptide and identify the protein from which the detected peptide was derived. When the detected peptide is a signature peptide, the method preferably includes determining the mass of the signature peptide and using the mass of the signature peptide to identify the protein from which the detected peptide was derived. The invention thus makes it possible to identify a protein in a sample, preferably a complex sample, without sequencing the entire protein. In many cases the method allows for identification of a protein in a sample without sequencing any part of the protein. In a preferred embodiment, the mass of the signature peptide compared with the masses of reference peptides derived from putative proteolytic cleavage of a plurality of reference proteins in a database, wherein the mass of the references peptides are adjusted to include the mass of the affinity ligand, if necessary. Prior to making this comparison, reference peptides are optionally computationally selected to exclude those that do not contain an amino acid upon which the affinity selection is based in order to simplify the database comparison. Optionally, the amino acid sequence of the detected peptide can be determined and used to identify the protein from which the detected peptide was derived.

When a protein or peptide is present in a one sample but not in another sample, it can be difficult to determine which sample generated the single peak observed during mass spectrometric analysis of the combined sample. This problem is addressed by double labeling the first sample, either before or after proteolytic cleavage, with two different isotopes or two different numbers of heavy atoms. The first sample is partitioned into first and second subsamples, which are labeled with chemically equivalent moieties containing first and second isotopes or numbers of heavy atoms, respectively. Polypeptides in the second sample are labeled with a chemically equivalent moiety containing a third isotope or number of heavy atoms greater than in the other two cases. The first, second and third labeling agents are chemically equivalent yet isotopically distinct. Preferably, the labeling agents are acylating agents. The three samples are combined and optionally fractionating to yield a plurality of peptide fractions amenable to mass spectrometric isotope ratio analysis. The presence of a doublet during mass spectrometric analysis due to the presence of the first and second isotope labeling agents indicates the absence of the protein in the second sample, and the presence of a single peak due to the presence of the third isotope labeling agent indicates the absence of the protein in the first sample.

Sometimes a solution based fragmentation of a protein mixture generates two or more different peptides having identical mass and chromatographic separation properties ("isobaric peptides"), such as peptides with the same amino acid composition but different amino acid sequences. In this case, the composite mass spectrum will not reflect the isotope ratios of the individual peptides. However, the mass of one or more of the constituent fragment ions generated during gas phase fragmentation of the peptide will be different. These fragment ions can therefore be resolved by subjecting the precursor ions to a second dimension of mass spectrometry, provided the peptides are isotopically labeled at either the N- or the C-terminus. Isotopic peaks from the first dimension spanning a mass range of up to about 20 amu are selected for mass spectrometric analysis in the second dimension. Fragmentation prior to the second dimension of mass spectrometry can occur by either post-source decay or collision-induced (or collision-activated) dissociation (CID or CAD) of the precursor ion. The isotope ratio of those fragment ions that differ between peptides can be used to quantify the peptides.

This problem is not limited to isobaric peptides. When the difference between the masses of the labeling agents is 3 amu a problem will occur any time the peptide clusters are within 6 amu of each other such that they overlap. A range of isotope peaks, for example about 6 to about 10 amu range for deuterium labeled peptides, is selected for mass spectrometric analysis in the second dimension, and unique fragment ions can be located. When a broader mass window is selected for use in the second dimension for deuterated samples, $^2H_3$ and $^1H_3$ N-acetyl labeled forms of the peptide will both be present in the second dimension, and the $^2H_3$ and $^1H_3$ labeling will only be found on the fragment ions that contain portions of the molecule that were acetylated. Quantification can be achieved by measuring the $^2H_3$ and $^1H_3$ ratio in the second dimension.

The methods for protein identification and, optionally, quantification described herein offer the investigator a high degree of experimental flexibility and are also very amenable to automation. They are, in addition, extremely sensitive; for example, the use of mass spectrometry to uniquely define the signature peptide (by its mass) makes it possible for the isotope labeling method of the invention to distinguish among single site protein polymorphisms.

It should be noted that, while isotope labeling of the proteins or constituent peptides is useful for quantification and quantitative comparison of proteins and/or peptides in a complex mixture, isotope labeling is not necessary to identify proteins in a complex mixture. A protein can be identified by comparing the mass of a signature peptide to the masses of peptides in a peptide database formed from computational cleavage of a set of proteins. The absence of the need to isotopically label the protein or peptides facilitates automation and also makes protein identification using database searching algorithms easier, since the peptides do not include the mass of an exogenous isotope labeling reagent.

The terms "a", "an", "the", and "at least one" include the singular as well as the plural unless specified to the contrary.

BRIEF DESCRIPTION OF THE DRAWINGS

Figure 1:
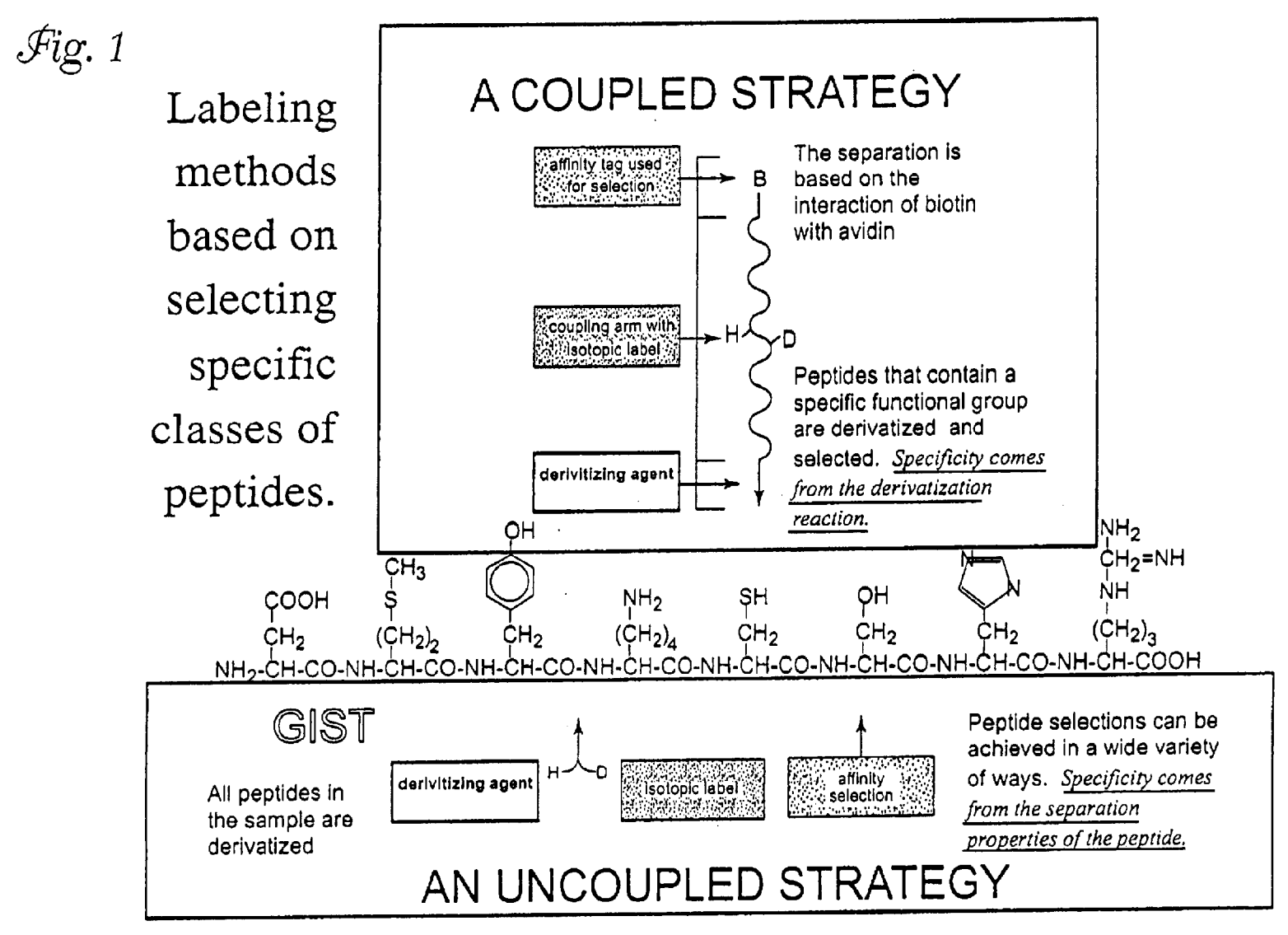

FIG. 1 is a schematic representation of coupled and uncoupled methods of the invention.

DETAILED DESCRIPTION OF THE INVENTION

Figure 2:
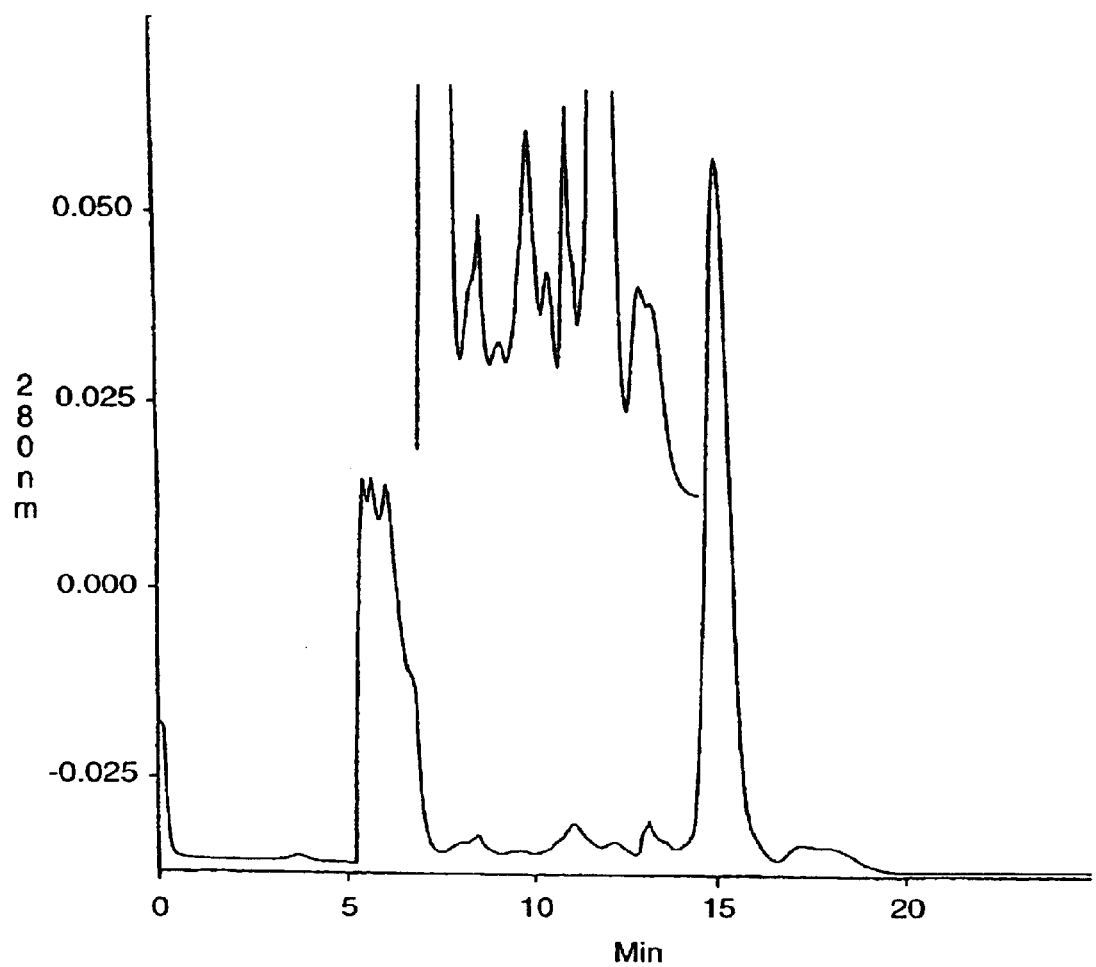
FIG. 2 is a reversed-phase chromatogram of proteins isolated from bovine nuclei by chromatography on a *Bandeiraea simplicifolia* (BS-II) lectin affinity column. Elution was achieved using a 0.20 M solution of N-acetylglucosamine.

Roughly 90% of the time, the amino acid sequence of a peptide fragment having a mass of over 500 daltons will be unique to the protein from which it is derived. This varies somewhat with the organism. Because of this uniqueness, these peptides are referred to herein as "signature peptides." Signature peptides are often, but not always, characterized by features such as low abundance amino acids such as cysteine or histidine, phosphorylation or glycosylation, and antigenic properties. If one were to select from a pool of all tryptic peptides produced from proteolysis of the proteome those peptides that contain the low abundance amino acids histidine or cysteine, there would be between one and four "signature peptides" per protein. The number depends to some extent on the size of the protein.

A signature peptide is a peptide that is unique to a single protein and preferably contains about 6 to about 20 amino acids. Enzymatic digestion of a complex mixture of proteins will therefore generate peptides, including signature peptides, that can theoretically be used to identify particular proteins in the complex mixture. Indeed, liquid chromatography, capillary electrophoresis, and mass spectrometry are much more adept at the analysis of peptides than the intact proteins from which they are derived. A complex mixture of proteins preferably contains at least about 100 proteins, more preferably it contains at least about 1000 proteins and it can contain several thousand proteins. However, when a complex mixture containing thousands of proteins is proteolytically digested, it is probable that a hundred thousand or more peptides will be generated during proteolysis. This is beyond the resolving power of liquid chromatography and mass spectrometry systems.

This problem is solved in the present invention by utilizing a selection, preferably an affinity selection, after the proteolytic cleavage to select peptide fragments that contain specific amino acids, thereby substantially reducing the number of sample components that must be subjected to further analysis. The method for protein identification of the invention is well-suited to the identification of proteins in a complex mixture, and at a minimum includes proteolytic cleavage of a protein and affinity selection of the peptides. The affinity selection can be effected using an affinity ligand that has been covalently attached to the protein (prior to cleavage) or its constituent peptides (after cleavage), or using an endogenous affinity ligand. The affinity selection is preferably based on low abundance amino acids or post-translational modifications so as to preferentially isolate "signature peptides." The method is not limited by the affinity selection method(s) employed and nonlimiting examples of affinity selections are described herein and can also be found in the scientific literature, for example in M. Wilchek, *Meth. Enzymol.* 34, 182–195 (1974). This approach enormously reduces the complexity of the mixture. If desired, two or more affinity ligands (e.g., primary and secondary affinity ligands) can be used, thereby allowing a finer selection. Illustrative examples of pre- and post-digestion labeling are shown in Examples IV and V, below.

Preferably, the affinity selected peptides are subjected to a fractionation step to reduce sample size prior to the determination of peptide masses. A premise of the signature peptide strategy is that many more peptides are generated during proteolysis than are needed for protein identification. This assumption means that large numbers of peptides potentially can be eliminated, while still leaving enough for protein identification.

The method is not limited by the techniques used for selection and/or fractionation. Typically, fractionation is carried out using single or multidimensional chromatography such as reversed phase chromatography (RPC), ion exchange chromatography, hydrophobic interaction chromatography, size exclusion chromatography, or affinity fractionation such as immunoaffinity and immobilized metal affinity chromatography. Preferably the fractionation involves surface-mediated selection strategies. Electrophoresis, either slab gel or capillary electrophoresis, can also be used to fractionate the peptides. Examples of slab gel electrophoretic methods include sodium dodecyl sulfate polyacrylamide gel electrophoresis (SDS-PAGE) and native gel electrophoresis. Capillary electrophoresis methods that can be used for fractionation include capillary gel electrophoresis (CGE), capillary zone electrophoresis (CZE) and capillary electrochromatography (CEC), capillary iso-electric focusing, immobilized metal affinity chromatography and affinity electrophoresis.

Masses of the affinity-selected peptides, which include the "signature peptides," are preferably determined by mass spectrometry, preferably using matrix assisted laser desorption ionization (MALDI) or electrospray ionization (ESI), and mass of the peptides is analyzed using time-of-flight (TOF), quadrapole, ion trap, magnetic sector or ion cyclotron resonance mass analyzers, or a combination thereof including, without limitation, TOF-TOF and other combinations. Preferably the mass of the peptides is determined with a mass accuracy of about 10 ppm or better; more preferably, masses are determined with a mass accuracy of about 5 ppm or better; most preferably they are determined with a mass accuracy of about 1 ppm or better. The lower the ppm value, the more accurate the mass determination and the less sequence data is needed for peptide identification.

It should be understood that the term "protein," as used herein, refers to a polymer of amino acids and does not connote a specific length of a polymer of amino acids. Thus, for example, the terms oligopeptide, polypeptide, and enzyme are included within the definition of protein, whether produced using recombinant techniques, chemical or enzymatic synthesis, or naturally occurring. This term also includes polypeptides that have been modified or derivatized, such as by glycosylation, acetylation, phosphorylation, and the like. When the term "peptide" is used herein, it generally refers to a protein fragment produced in solution.

Selection of Sample

The method of the invention is designed for use in complex samples containing a number of different proteins. Preferably the sample contains at least about two proteins; more preferably it contains at least about 100 proteins; still more preferably it contains at least about 1000 proteins. A sample can therefore include total cellular protein or some fraction thereof. For example, a sample can be obtained from a particular cellular compartment or organelle, using methods such as centrifugal fractionation. The sample can be derived from any type of cell, organism, tissue, organ, or bodily fluid, without limitation. The method of the invention can be used to identify one or more proteins in the sample, and is typically used to identify multiple proteins in a single complex mixture. It should therefore be understood that when the method of the invention is referred to, for simplicity, as a method for identifying "a protein" in a mixture that contains multiple proteins, the term "a protein"

is intended to mean "at least one protein" and thus includes one or more proteins.

Fragmentation of Proteins

Fragmentation of proteins can be achieved by chemical, enzymatic or physical means, including, for example, sonication or shearing. Preferably, a protease enzyme is used, such as trypsin, chymotrypsin, papain, gluc-C, endo lys-C, proteinase K, carboxypeptidase, calpain, subtilisin and pepsin; more preferably, a trypsin digest is performed. Alternatively, chemical agents such as cyanogen bromide can be used to effect proteolysis. The proteolytic agent can be immobilized in or on a support, or can be free in solution.

Selecting Peptides with Specific Amino Acids

Peptides from complex proteolytic digests that contain low abundance amino acids or specific post-translational modifications are selected (purified) to reduce sample complexity while at the same time aiding in the identification of peptides selected from the mixture. Selection of peptide fragments that contain cysteine, tryptophan, histidine, methionine, tyrosine, tyrosine phosphate, serine and threonine phosphate, O-linked oligosaccharides, or N-linked oligosaccharides, or any combination thereof can be achieved. It is also possible to determine whether the peptide has a C-terminal lysine or arginine and at least one other amino acid.

The present invention thus provides for selection of proteolytic cleavage fragments that contain these specific amino acids or post-translational modifications, and includes a method of purifying individual peptides sufficiently that they are amenable to MALDI mass spectrometry (MALDI-MS). In view of the fact that MALDI-MS can accommodate samples with 50–150 peptides and a good reversed phase chromatography (RPC) column can produce 200 peaks, a high quality RPC-MALDI-MS system can be expected to analyze a mixture of 10,000 to 30,000 peptides. Preliminary studies by others with less powerful RPC-electrospray-MS systems support this conclusion (F. Hsieh et al., *Anal. Chem.* 70:1847–1852 (1998)). Selection of ten or less peptides from each protein would allow this system to deal with mixtures of 1,000 to 3,000 proteins in the worst case scenario. More stringent selection would increase this number. The selection method chosen is thus very important.

Affinity Tags

An affinity tag used for selection can be endogenous to the protein, or it can be added by chemical or enzymatic processes. The term "affinity tag," as used herein, refers to a chemical moiety that functions as, or contains, an affinity ligand that is capable of binding (preferably noncovalently, but covalent linkages are contemplated also) to a second, "capture" chemical moiety, such that a protein or peptide that naturally contains or is derivatized to include the affinity tag can be selected (or "captured") from a pool of proteins or peptides by contacting the pool with the capture moiety. The capture moiety is preferably bound to a support surface, preferably a porous support surface, as a stationary phase. Examples of suitable supports include porous silica, porous titania, porous zirconia, porous organic polymers, porous polysaccharides, or any of these supports in non-porous form.

Preferably the interactions between the affinity tag and the capture moiety are specific and reversible (e.g., noncovalent binding or hydrolyzable covalent linkage), but they can, if desired, initially be, or subsequently be made, irreversible (e.g., a nonhydrolyzable covalent linkage between the affinity tag and the capture moiety). It is important to understand that the invention is not limited to the use of any particular affinity ligand.

Examples of endogenous affinity ligands include naturally occurring amino acids such as cysteine (selected with, for example, an acylating reagent) and histidine, as well as carbohydrate and phosphate moieties. A portion of the protein or peptide amino acid sequence that defines an antigen can also serve as an endogenous affinity ligand, which is particularly useful if the endogenous amino acid sequence is common to more than one protein in the original mixture. In that case, a polyclonal or monoclonal antibody that selects for families of polypeptides that contain the endogenous antigenic sequence can be used as the capture moiety. An antigen is a substance that reacts with products of an immune response stimulated by a specific immunogen, including antibodies and/or T lymphocytes. As is known in the art, an antibody molecule or a T lymphocyte may bind to various substances, for example, sugars, lipids, intermediary metabolites, autocoids, hormones, complex carbohydrates, phospholipids, nucleic acids, and proteins. As used herein, the term "antigen" means any substance present in a peptide that may be captured by binding to an antibody, a T lymphocyte, the binding portion of an antibody or the binding portion of T lymphocyte.

A non-endogenous (i.e., exogenous) affinity tag can be added to a protein or peptide by, for example, first covalently linking the affinity ligand to a derivatizing agent to form an affinity tag, then using the affinity tag to derivatize at least one functional group on the protein or peptide. Alternatively, the protein or peptide can be first derivatized with the derivatizing agent, then the affinity ligand can be covalently linked to the derivatized protein or peptide at a site on the derivatizing agent. An example of an affinity ligand that can be covalently linked to a protein or peptide by way chemical or enzymatic derivatization is a peptide, preferably a peptide antigen or polyhistidine. A peptide antigen can itself be derivatized with, for example, a 2,4-dinitrophenyl or fluorescein moiety, which renders the peptide more antigenic. A peptide antigen can be conveniently captured by an immunosorbant that contains a bound monoclonal or polyclonal antibody specific for the peptide antigen. A polyhistidine tag, on the other hand, is typically captured by an IMAC column containing a metal chelating agent loaded with nickel or copper. Biotin, preferably ethylenediamine terminated biotin, which can be captured by the natural receptor avidin, represents another affinity ligand. Other natural receptors can also be used as capture moieties in embodiments wherein their ligands serve as affinity ligands. Other affinity ligands include dinitrophenol (which is typically captured using an antibody or a molecularly imprinted polymer), short oligonucleotides, and polypeptide nucleic acids (PNA) (which are typically captured by nucleic acid hybridization). Molecularly imprinted polymers can also be used to capture. The affinity ligand is typically linked to a chemical moiety that is capable of derivatizing a selected functional group on a peptide or protein, to form an affinity tag. An affinity ligand can, for example, be covalently linked to maleimide (a protein or peptide derivatizing agent) to yield an affinity tag, which is then used to derivatize the free sulfhydryl groups in cysteine, as further described below.

Selecting Cysteine-Containing Peptides

It is a common strategy to alkylate the sulfhydryl groups in a protein before proteolysis. Alkylation is generally based on two kinds of reactions. One is to alkylate with a reagent such as iodoacetic acid (IAA) or iodoacetamide (IAM). The other is to react with vinyl pyridine, maleic acid, or N-ethylmaleimide (NEM). This second derivatization method is based on the propensity of —SH groups to add to the C=C double bond in a conjugated system. Alkylating agents linked to an affinity ligand double as affinity tags and can be used to select cysteine containing peptides after, or concomitant with, alkylation. For example, affinity-tagged iodoacetic acid is a convenient selection for cysteine.

Optionally, the protein is reduced prior to alkylation to convert all the disulfides (cystines) into sulfhydryls (cysteines) prior to derivatization. Alkylation can be performed either prior to reduction (permitting the capture of only those fragments in which the cysteine is free in the native protein) or after reduction (permitting capture of the larger group containing all cysteine-containing peptides, include those that are in the oxidized cystine form in the native protein).

Preparation of an affinity tagged N-ethylmaleimide may be achieved by the addition of a primary amine-containing affinity tag to maleic anhydride. The actual affinity tag may be chosen from among a number of species ranging from peptide antigens, polyhistidine, biotin, dinitrophenol, or polypeptide nucleic acids (PNA). Peptide and dinitrophenol tags are typically selected with an antibody whereas the biotin tag is selected with avidin. When the affinity tag includes as the affinity ligand a peptide, and when proteolysis of the protein mixture is accomplished after derivatization using trypsin or lys-C, the peptide affinity ligand preferably does not contain lysine or arginine, so as to prevent the affinity ligand from also being cleaved during proteolysis. Biotin is a preferred affinity ligand because it is selected with very high affinity and can be captured with readily available avidin/streptavidin columns or magnetic beads. As noted above, polyhistidine tags are selected in an immobilized metal affinity chromatography (IMAC) capture step. This selection route has the advantage that the columns are much less expensive, they are of high capacity, and analytes are easily desorbed.

Alternatively, cysteine-containing peptides or proteins can be captured directly during alkylation without incorporating an affinity ligand into the alkylating agent. An alkylating agent is immobilized on a suitable substrate, and the protein or peptide mixture is contacted with the immobilized alkylating agent to select cysteine-containing peptides or proteins. If proteins are selected, proteolysis can be conveniently carried out on the immobilized proteins to yield immobilized cysteine-containing peptides. Selected peptides or proteins are then released from the substrate and subjected to further processing in accordance with the method of the invention.

When alkylation is done in solution, excess affinity tagged alkylating agent is removed prior to selection with an immobilized capture moiety. Failure to do so will severely reduce the capacity of the capture sorbent. This is because the tagged alkylating agent is used in great excess and the affinity sorbent cannot discriminate between excess reagent and tagged peptides. This problem is readily circumvented by using a small size exclusion column to separate alkylated proteins from excess reagent prior to affinity selection. The whole process can be automated (as further described below) by using a multidimensional chromatography system with, for example, a size exclusion column, an immobilized trypsin column, an affinity selector column, and a reversed phase column. After size discrimination the protein is valved through the trypsin column and the peptides in the effluent passed directly to the affinity column for selection. After capture and concentration on the affinity column, tagged peptides are desorbed from the affinity column and transferred to the reversed phase column where they were again captured and concentrated. Finally, the peptides are eluted with a volatile mobile phase and fractions collected for mass spectral analysis. Automation in this manner has been found to work well.

Selecting Tyrosine-Containing Peptides

Like cysteine, tyrosine is an amino acid that is present in proteins in limited abundance. It is known that diazonium salts add to the aromatic ring of tyrosine ortho to the hydroxyl groups; this fact has been widely exploited in the immobilization of proteins through tyrosine. Accordingly, tyrosine-containing peptides or proteins can be affinity-selected by derivatizing them with a diazonium salt that has been coupled at its carboxyl group to a primary amine on an affinity ligand, for example through the α-amino group on a peptide tag as described above. Alternatively, that diazonium salt can be immobilized on a suitable substrate, and the protein or peptide mixture is contacted with the immobilized diazonium salt to select tyrosine-containing peptides or proteins. If proteins are selected, proteolysis can be conveniently carried out on the immobilized proteins to yield immobilized tyrosine-containing peptides. Selected peptides or proteins are then released from the substrate and subjected to further processing in accordance with the method of the invention.

Selecting Tryptophan-Containing Peptides

Tryptophan is present in most mammalian proteins at a level of <3%. This means that the average protein will yield only a few tryptophan containing peptides. Selective derivatization of tryptophan has been achieved with 2,4-dinitrophenylsulfenyl chloride at pH 5.0 (M. Wilcheck et al., Biochem. Biophys. Acta 178:1–7 (1972)). Using an antibody directed against 2,4-dinitrophenol, an immunosorbant was prepared to select peptides with this label. The advantage of tryptophan selection is that the number of peptides will generally be small.

Selecting Histidine-Containing Peptides.

In view of the higher frequency of histidine in proteins, it would seem at first that far too many peptides would be selected to be useful. The great strength of the procedure outlined below is that it selects on the basis of the number of histidines, not just the presence of histidine. Immobilized metal affinity chromatography (IMAC) columns loaded with copper easily produce ten or more peaks. The fact that a few other amino acids are weakly selected is not a problem, and the specificity of histidine selection can, if desired, be greatly improved by acetylation of primary amino groups. Fractions from the IMAC column are transferred to an RPC-MALDI/MS system for analysis. The number of peptides that can potentially be analyzed jumps to 100,000–300,000 in the IMAC approach. An automated IMAC-RPC-MALDI/MS system essentially identical to that used for cysteine selection has been assembled. The only difference is in substituting an IMAC column for the affinity sorbent and changes in the elution protocol. Gradient elution in these systems is most easily achieved by applying step gradients to the affinity column. After reduction, alkylation, and digestion, the peptide mixture is captured on the IMAC column loaded with copper. Peptides are isocratically eluted from the IMAC using imidazole or a change in pH, and directly transferred to the RPC column where they are concentrated at the head of the column. The IMAC is then taken off line, the solvent lines of the instrument purged at 10 ml/minute for a few seconds with RPC solvent A, and then the RPC column is gradient eluted and column fractions collected for MALDI-MS. When this is done, the RPC column is recycled with the next solvent for step elution of the IMAC column, the IMAC column is then brought back on line, and the second set of peptides is isocratically eluted from the IMAC column and transferred to the RPC column where they are readsorbed. The IMAC column is again taken off-line, the system purged, and the second set of peptides is eluted from the RPC column. This process is repeated until the IMAC column has been eluted. Again, everything leading up to MALDI-MS is automated.

Selecting Post-Translationally Modified Proteins.

Post-translational modification plays an important role in regulation. For this reason, it is necessary to have methods that detect specific post-translational modifications. Advantageously, the method of the invention can distinguish among proteins having a single signature peptide where speciation occurs by post-translational modification, if the affinity ligand is associated with, or constitutes, the post-translational moiety (e.g., sugar residue or phosphate). Among the more important post-translational modifications are i) the phosphorylation of tyrosine, serine, or threonine; ii) N-glycosylation; and iii) O-glycosylation.

Selecting Phosphoproteins

In the case of phosphorylated proteins, such as those containing phosphotyrosine and phosphoserine, selection can achieved with monoclonal antibodies that target specific phosphorylated amino acids. For example, immunosorbant columns loaded with a tyrosine phosphate specific monoclonal antibody are commercially available. Preferably, all proteins in a sample are digested, then the immunosorbant is used to select only the tyrosine phosphate containing peptides. As in other selection schemes, these peptides can separated by reversed phase chromatography and subjected to MALDI.

Alternatively, selection of phosphopeptides can be achieved using IMAC columns loaded with gallium (M. Posewitz et al., *Anal. Chem.* 71(14):2883–2992 (1999)). Phosphopeptides can also be selected using anion exchange chromatography, preferably on a cationic support surface, at acidic pH.

In addition, because zirconate sorbents have high affinity for phosphate containing compounds (C. Dunlap et al., *J. Chromatogr. A* 746:199–210 (1996)), zirconia-containing chromatography is expected to be suitable for the purification of phosphoproteins and phosphopeptides. Zirconate clad silica sorbents can be prepared by applying zirconyl chloride dissolved in 2,4-pentadione to 500 angstrom pore diameter silica and then heat treating the support at 400° C. Another alternative is the porous zirconate support recently described by Peter Carr (C. Dunlap et al., *J. Chromatogr. A* 746:199–210 (1996)). Phosphopeptides are eluted using a phosphate buffer gradient. In many respects, this strategy is the same as that of the IMAC columns.

Selecting O-Linked Oligosaccharide Containing Peptides

Glycopeptides can be selected using lectins. For example, lectin from *Bandeiraea simplicifolia* (BS-II) binds readily to proteins containing N-acetylglucosamine. This lectin is immobilized on a silica support and used to affinity select O-glycosylated proteins, such transcription factors, containing N-acetylglucosamine and the glycopeptides resulting from proteolysis. The protocol is essentially identical to the other affinity selection methods described above. Following reduction and alkylation, low molecular weight reagents are separated from proteins. The proteins are then tryptic digested, the glycopeptides selected on the affinity column, and then the glycopeptides resolved by RPC. In the case of some transcription factors, glycosylation is homogeneous and MALDI-MS of the intact glycopeptide is unambiguous. That is not the case with the more complex O-linked glycopeptides obtained from many other systems. Heterogeneity of glycosylation at a particular serine will produce a complex mass spectrum that is difficult to interpret. Enzymatic deglycosylation of peptides subsequent to affinity selection is indicated in these cases. Deglycosylation can also be achieved chemically with strong base and is followed by size exclusion chromatography to separate the peptides from the cleaved oligosaccharides.

It is important to note that O-linked and N-linked glycopeptides are easily differentiated by selective cleavage of serine linked oligosaccharides (E. Roquemore et al., *Meth. Enzymol.* 230:443–460 (1994)). There are multiple ways to chemically differentiate between these two classes of glycopeptides. For example, basic conditions in which the hemiacetal linkage to serine is readily cleaved can be utilized. In the process, serine is dehydrated to form an $\alpha,\beta$ unsaturated system (C=C—C=O). The C=C bond of this system may be either reduced with $NaBH_4$ or alkylated with a tagged thiol for further affinity selection. This would allow O-linked glycopeptides to be selected in the presence of N-linked glycopeptides. The same result could be achieved with enzymatic digestion.

Selecting N-Linked Oligosaccharide-Containing Peptides

As with O-linked oligosaccharide-containing peptides, lectins can be used to affinity select N-linked glycopeptides following reductive alkylation and proteolysis. To avoid selecting O-linked glycopeptides, the peptide mixture is subjected to conditions that cause selective cleavage O-linked oligosaccharides prior to affinity selection using the lectin. Preferably O-linked deglycosylation is achieved using a base treatment after reductive alkylation, followed by size exclusion chromatography to separate the peptides from the cleaved oligosaccharides. To address the potential problem of heterogeneity of glycosylation, and N-linked glycopeptides are deglycosylated after selection. Automation can be achieved with immobilized enzymes, but long residence times in the enzyme columns are needed for the three enzymatic hydrolysis steps.

Identification of Signature Peptides and Their Parent Proteins

After peptides of interest are detected using mass spectrometry, the protein from which a peptide originated is determined. In most instances this can be accomplished using a standard protocol that involves scanning either protein or DNA databases for amino acid sequences that would correspond to the proteolytic fragments generated experimentally, matching the mass of all possible fragments against the experimental data (F. Hsieh et al., *Anal. Chem.* 70:1847–1852 (1998); D. Reiber et all, *Anal. Chem* 70:673–683 (1998)). When a DNA database is used as a reference database, open reading frames are translated and the resulting putative proteins are cleaved computationally to generate the reference fragments, using the same cleavage method that was used experimentally. Likewise, when a protein database is used, proteolytic cleavage is also performed computationally to generate the reference fragments. In addition, masses of the reference peptide fragments are adjusted as necessary to reflect derivatizations equivalent to those made to the experimental peptides, for example to include the exogenous affinity tag. The presence of signature peptides in the sample is detected by comparing the masses of the experimentally generated peptides with the masses of signature peptides derived from putative proteolytic cleavage of the set of reference proteins obtained from the database. Software and databases suited to this purpose are readily available either through commercial mass spectrometer software and the Internet. Optionally, the peptide databases can be preselected or reduced in complexity by removing peptides that do not contain the amino acid(s) upon which affinity selection is based.

There will, of course, be instances where peptides cannot be identified from databases or when multiple peptides in the database have the same mass. One approach to this problem is to sequence the peptide in the mass spectrometer by collision induced dissociation. Ideally this is done with a MALDI-MS/MS or ESI-MS/MS instrument. Another way to proceed is to isolate peptides and sequence them by a conventional method. Because the signature peptide strategy is based on chromatographic separation methods, it is generally relatively easy to purify peptides for amino acid sequencing if sufficient material is available. For example, conventional PTH-based sequencing or carboxypeptidase based C-terminal sequencing described for MALDI-MS several years ago (D. Patterson et al., *Anal. Chem.* 67:3971–3978 (1995)). In cases where 6–10 amino acids can be sequenced from the C-terminus of a peptide, it is often possible to synthesize DNA probes that would allow selective amplification of the cDNA complement along with DNA sequencing to arrive at the structure of the protein.

Internal Standard Quantification with Signature Peptides

There is a growing need to move beyond the massive effort to define genetic and protein components of biological systems to the study of how they and other cellular metabolites are regulated and respond to stimuli. The words "stimulus" and "stimuli" are used broadly herein and mean any agent, event, change in conditions or even the simple passage of time that may be associated with a detectable change in expression of at least one metabolite within a cell, without limitation. For example, a stimulus can be a change in growth conditions, pH, nutrient supply, or temperature; contact with an exogenous agent such as a drug or microbe, competition with another organism, and the like. The term "metabolite" refers, in this context, to a cellular component, preferably an organic cellular component, which can change in concentration in response to a stimulus, and includes large biomolecules such as proteins, polynucleotides, carbohydrates and fats, as well as small organic molecules such as hormones, peptides, cofactors and the like.

Accordingly, in this aspect of the invention post-biosynthetic isotope labeling of cellular metabolites, preferably proteins and peptides, is utilized to detect cellular components that are up and/or down regulated in comparison to control environments. Metabolites, such as proteins (or peptides if proteolysis is employed) in control and experimental samples are post-synthetically derivatized with distinct isotopic forms of a labeling agent and mixed before analysis. Preferably, the samples are obtained from a "biological environment," which is to be broadly interpreted to include any type of biological system in which enzymatic reactions can occur, including in vitro environments, cell culture, cells at any developmental stage, whole organisms, organs, tissues, bodily fluids, and the like. As between the two samples, labeled metabolites are chemically equivalent but isotopically distinct. In this context, chemical equivalence is defined by identical chromatographic and electrophoretic behavior, such that the two metabolites cannot be separated from each other using standard laboratory purification and separation techniques. For example, a protein or peptide present in each sample may, after labeling, differ in mass by a few atomic mass units when the protein or peptide from one sample is compared to the same protein or peptide from the other sample (i.e., they are isotopically distinct). However, these two proteins or peptides would ideally be chemically equivalent as evidenced by their identical chromatographic behavior and electrophoretic migration patterns.

Because >95% of cellular proteins do not change in response to a stimulus, proteins (as well as other metabolites) in flux can be readily identified by isotope ratio changes in species resolved, for example, by 2-D gel electrophoresis or 2-D chromatography. Once these proteins are detected, they can optionally be identified using the "signature peptide" approach as described herein or any other convenient method. One example of how this method of the invention can be used is to analyze patterns of protein expression in a breast cancer cell before and after exposure to a candidate drug. The method can also be used to analyze changes in protein expression patterns in a cell or an organism as a result of exposure to a harmful agent. As yet another example, the method can be used to track the changes in protein expression levels in a cell as it is exposed, over time, to changes in light, temperature, electromagnetic field, sound, humidity, and the like.

The internal standard method of quantification is based on the concept that the concentration of an analyte ($A$) in a complex mixture of substances may be determined by adding a known amount of a very similar, but distinguishable substance ($\Lambda$) to the solution and determining the concentration of $A$ relative to $\Lambda$. Assuming that the relative molar response ($\mathfrak{R}$) of the detection system for these two substances is known, then $$[A] = [\Lambda] \mathfrak{R} \Delta$$

The term $\Delta$ is the relative concentration of $A$ to that of the internal standard $\Lambda$ and is widely used in analytical chemistry for quantitative analysis. It is important that $A$ and $\Lambda$ are as similar as possible in chemical properties so that they will behave the same way in all the steps of the analysis. It would be very undesirable for $A$ and $\Lambda$ to separate. One of the best ways to assure a high level of behavioral equivalency is to isotopically label either the internal standard ($\Lambda$) or the analyte ($A$).

As noted above, it is difficult to determine whether a regulatory stimulus has caused a single, or a small group of proteins in a complex mixture to increase or decrease in concentration relative to other proteins in the sample. Determining the magnitude of this change is an even more difficult problem. The internal standard method apparently cannot be applied here because i) the analytes $A_{1-n}$ undergoing change are of unknown structure and ii) it would be difficult to select internal standards $\Lambda_{1-n}$ of nearly identical properties.

Post-synthetic isotope labeling of proteins in accordance with the method of the invention advantageously creates internal standards from proteins of unknown structure and concentration. Whenever there is a control, or reference state, in which the concentration of proteins is at some reference level, proteins in this control state can serve as internal standards. In a preferred embodiment, constituent peptides are labeled after fragmentation of the proteins in the sample. The timing of the labeling step provides an opportunity to label every peptide in the mixture by choosing a labeling method that labels at the N or the C terminus of a polypeptide. Application of the labeling method of the invention after the proteins have been synthesized has a further advantage. Although metabolic incorporation of labeled amino acids has been widely used to label proteins, it is not very reproducible and is objectionable in human subjects. Post-sampling strategies for incorporation of labels are much more attractive.

A key advantage of the isotope labeling method of the invention is that it detects relative change, not changes in absolute amounts of analytes. It is very difficult to determine changes in absolute amounts analytes that are present at very low levels. This method is as sensitive to changes in very dilute analytes as it is those that are present at great abundance. Another important advantage of this approach is that it is not influenced by quenching in the MALDI. This means that large number of peptides can be analyzed irrespective of the expected quenching.

The isotope labeling method of the invention allows identification of up- and down-regulated proteins using the affinity selection methods described above, 2-D gel electrophoresis, 1-D, 2-D or multi-dimensional chromatography, or any combination thereof, and employs either autoradiography or mass spectrometry. Examples of radioisotopes and stable mass isotopes that can be used to label a metabolite post-biosynthetically include $^2$H, $^3$H, $^{13}$C, $^{14}$C, $^{15}$N, $^{17}$O, $^{18}$O, $^{32}$P, $^{33}$S, $^{34}$S and $^{35}$S, but should be understood that the invention is in no way limited by the choice of isotope. An isotope can be incorporated into an affinity tag, or it can be linked to the peptide or protein in a separate chemical or enzymatic reaction. It should be noted that affinity selection of peptides is an optional step in the isotope labeling method of the invention, thus the inclusion of an affinity ligand in the labeling agent is optional.

In one embodiment of the isotope labeling method, proteins are isotopically labeled prior to cleavage. Proteins in a control sample are derivatized with a labeling agent that contains an isotope, while proteins in an experimental sample are derivatized with the normal labeling agent. The samples are then combined. The derivatized proteins can be chemically or enzymatically cleaved either before or after separation. Cleavage is optional; isotopically labeled proteins can, if desired, be analyzed directly following a fractionation step such as multidimensional chromatography, 2-D electrophoresis or affinity fractionation. When the derivatized proteins are cleaved before separation, the labeling agent preferably contains an affinity ligand, and the tagged peptide fragments are first affinity selected, then fractionated in a 1-D or 2-D chromatography system, after which they are analyzed using mass spectrometry (MS). In instances where the derivatized proteins are cleaved after fractionation, 2-D gel electrophoresis is preferably used to separate the proteins. If the peptides have also been affinity labeled, selection of the affinity-tagged peptides can be performed either before or after electrophoresis. The objective of fractionation is to reduce sample complexity to the extent that isotope ratio analysis can be performed, using a mass spectrometer, on individual peptide pairs.

Mass spectrometric analysis can be used to determine peak intensities and quantitate isotope ratios in the combined sample, determine whether there has been a change in the concentration of a protein between two samples, and to facilitate identification of a protein from which a peptide fragment, preferably a signature peptide, is derived. Preferably, changes in peptide concentration between the control and experimental samples are determined by isotope ratio MALDI-mass spectrometry because MALDI-MS allows the analysis of more complex peptide mixtures, but ESI-MS may also be used when the peptide mixture is not as complex. In a complex combined mixture, there may be hundreds to thousands of peptides, and many of them will not change in concentration between the control and experimental samples. These peptides whose levels are unchanged are used to establish the normalized isotope ratio for peptides that were neither up nor down regulated. All peptides in which the isotope ratio exceeds this value are up regulated. In contrast, those in which the ratio decreases are down regulated. A difference in relative isotope ratio of a peptide pair, compared to peptide pairs derived from proteins that did not change in concentration, thus signals a protein whose expression level did change between the control and experimental samples. If the peptide characterized by an isotope ratio different from the normalized ratio is a signature peptide, this peptide can be used according to the method of the invention to identify the protein from which it was derived.

In another embodiment of the isotope labeling method of the invention, isotope labeling takes place after cleavage of the proteins in the two samples. Derivatization of the peptide fragments is accomplished using a labeling agent that preferably contains an affinity ligand. On the other hand, an affinity ligand can be attached to the peptides in a separate reaction, either before or after isotopic labeling. If attached after isotopic labeling, the affinity ligand can be attached before or after the samples are combined. The peptide fragments in the combined mixture are affinity selected, then optionally fractionated using a 1-D or multi-dimensional chromatography system, or a capillary or slab gel electrophoretic technique, after which they are analyzed using mass spectrometry. In instances where the peptides are not affinity tagged, they are either affinity selected based on their inherent affinity for an immobilized ligand (preferably using IMAC or immobilized antibody or lectin) or analyzed without selection.

Alkylation with Isotopically Distinct Reagents

Proteins in control and experimental samples can be alkylated using different isotopically labeled iodoacetic acid ($ICH_2COOH$) subsequent to reduction. In the case of radionuclide derivatized samples, the control is, for example, derivatized with $^{14}$C labeled iodoacetic acid and the experimental sample with $^3$H labeled iodoacetate. Polypeptides thus labeled can be resolved by 2-D gel electrophoresis, as described in more detail below. When mass spectrometry is used in detection, normal iodoacetate can be used to derivatize the control and deuterated iodoacetate the experimental sample.

Based on the fact that proteins from control and experimental samples are identical in all respects except the isotopic content of the iodoacetate alkylating agent, their relative molar response ($\Re$) is expected to be 1. This has several important ramifications. When control and experimental samples are mixed:

$$A = \Lambda \Delta$$

In this case $\Delta$ will be i) the same for all the proteins in the mixture that do not change concentration in the experimental sample and ii) a function of the relative sample volumes mixed. If the protein concentration in the two samples is the same and they are mixed in a 1/1 ratio for example, then $\Delta=1$. With a cellular extract of 20,000 proteins, $\Delta$ will probably be the same for >19,900 of the proteins in the mixture. The concentration of a regulated protein that is either up- or down-regulated is expressed by the equation:

$$A_{exptl} = A_{contl} \Delta \delta$$

where $A_{exptl}$ is a protein from the experimental sample that has been synthetically labeled with a derivatizing agent, $A_{contl}$ is the same protein from the control sample labeled with a different isotopic form of the derivatizing agent, and $\delta$ is the relative degree of up- or down-regulation. Because $\Delta$ is an easily determined constant derived from the concentration ratio of probably >95% of the proteins in a sample, $\delta$ is readily calculated and proteins in regulatory flux easily identified.

Isotopic Labeling of Amines

If not included as part of the alkylating agent, an isotope label can be applied to the peptide as part of an affinity tag (if affinity selection is contemplated), or at some other reactive site on the peptide. Although application of the internal standard isotopic label in the affinity tag is operationally simpler and, in some cases, more desirable, it requires that each affinity tag be synthesized in at least two isotopic forms. Amine-labeling in a separate step (i.e., uncoupling the label and the affinity ligand) is therefore a preferred alternative.

Peptides that are generated by trypsin digestion (as well as those generated by many other types of cleavage reactions) have a primary amino group at their amino-terminus in all cases except those in which the peptide originated from a blocked amino-terminus of a protein. Moreover, the specificity of trypsin cleavage dictates that the C-terminus of signature peptides will have either a lysine or arginine (except the C-terminal peptide from the protein). In rare cases there may also be a lysine or arginine adjacent to the C-terminus. Primary amino groups are easily acylated with, for example, acetyl N-hydroxysuccinimide (ANHS). Thus, control samples can be acetylated with normal ANHS whereas experimental tryptic digests can be acylated with either $^{13}CH_3CO$—NHS or $CD_3CO$—NHS. Our studies show that the $\epsilon$-amino group of all lysines can be derivatized in addition to the amino-terminus of the peptide, as expected. This is actually an advantage in that it allows a determination of the number of lysine residues in the peptide.

Essentially all peptides in both samples will be derivatized and hence distinguishable from their counterparts using mass spectrometry. This means that any affinity selection method or combination of affinity selection methods (other than possibly those that select for arginine or lysine, which contain free amines) can be used at any point in the process to obtain a selected population enriched for signature peptides. For example, isotope labeling at amines can be used to identify changes in the relative amounts of peptides selected on the basis of cysteine, tryptophan, histidine, and a wide variety of post-translational modifications. In this preferred embodiment of the method, isotopic labeling and affinity labeling are two independent and distinct steps, and virtually all peptides are isotopically labeled. This provides significantly more flexibility and greater control over the production of signature peptides than is possible when the alkylating agent doubles as the isotope labeling agent.

Isotopic Labeling of Hydroxyls and Other Functional Groups

While acetylation is a convenient labeling method for proteins and their constituent peptides, other labeling methods may be useful for other types of cellular metabolites. For example, acetic anhydride can be used to acetylate hydroxyl groups in the samples, and trimethylchlorosilane can be used for less specific labeling of functional groups including hydroxyl groups, carboxylate groups and amines.

Interpretation of the Spectra

Isotopically labeled samples (control and experimental) are mixed, then subjected to mass spectrometry. In the case of labeled proteins (where no proteolytic cleavage is carried out), the proteins are typically separated using 2D-gel electrophoresis, multidimensional chromatography, or affinity fractionation such as immunoaffinity chromatography. Proteins from the control and experimental samples will comigrate, since neither isoelectric focusing (IEF), sodium dodecyl sulfate polyacrylamide gel electrophoresis (SDS-PAGE), nor chromatographic systems can resolve the isotopic forms of a protein. In the case of labeled peptides (whether or not affinity selected), peptides are optionally subjected to fractionation (typically using reversed phase chromatography or ion exchange chromatography) prior to analysis using mass spectrometry.

Radioisotope counting techniques can be used to discriminate between $^3H$ and $^{14}C$, and a mass spectrometer can readily differentiate between deuterated and normal species, either as proteolytic fragments or in the whole protein when it is of low (that is, under about 15 kD) molecular weight, allowing ratios of protein abundance between the two samples to be established. The relative abundance of most proteins will be the same and allow $\Delta$ to be calculated. A second group of proteins will be seen in which the relative abundance of specific proteins is much larger in the experimental sample. These are the up-regulated proteins. In contrast, a third group of proteins will be found in which the relative abundance of specific proteins is lower in the experimental sample. These are the down-regulated proteins. The degree ($\delta$) to which proteins are up- or down-regulated is calculated based on the computed value of $\Delta$ A more detailed analysis of the interpretation of the resulting mass spectra is provided using amine-labeled proteins as an example. Signature peptides of experimental samples in this example are acetylated at the amino-termini and on $\epsilon$-amino groups of lysines with either $^{13}CH_3CO$— or $CD_3CO$— residues, therefore any particular peptide will appear in the mass spectrum as a doublet. In the simplest case where i) trideutero-acetic acid is used as the labeling agent, ii) the C-terminus is arginine, iii) there are no other basic amino acids in the peptide, and iv) the control and experimental samples are mixed in exactly a 1/1 ratio before analysis, i.e., $\Delta=1$, the spectrum shows a doublet with peaks of approximately equal height separated by 3 amu. With 1 lysine the doublet peaks were separated by 6 amu and with 2 lysine by 9 amu. For each lysine that is added the difference in mass between the experimental and control would increase an additional 3 amu. It is unlikely in practice that mixing would be achieved in exactly a 1/1 ratio. Thus $\Delta$ will have to be determined for each sample and varies some between samples. Within a given sample, $\Delta$ will be the same for most peptides, as will also be the case in electrophoresis. Peptides that deviate to any extent from the average value of $\Delta$ are the ones of interest. The extent of this deviation is the value $\delta$, the degree of up- or down-regulation. As indicated above, $\Delta$ will be the same for greater than 95% of the proteins, or signature peptides in a sample.

As noted above, amino acids with other functional groups are occasionally labeled. In the presence of a large excess of acylating agent hydroxyl groups of serine, threonine, tyrosine, and carbohydrate residues in glycoconjugates and the imidazole group of histidine can also be derivatized. This does not interfere with quantification experiments, but complicates interpretation of mass spectra if groups other than primary amines are derivatized. In the case of hydroxyl groups, esters formed in the derivatization reaction are readily hydrolyzed by hydroxylamine under basic conditions. Aclylation of imadazole groups on the other hand occurs less frequently than esterification and is perhaps related to amino acid sequence around the histidine residue.

Another potential problem with the interpretation of mass spectra in the internal standard method of the invention can occur in cases where a protein is grossly up- or down-regulated. Under those circumstances, there will essentially be only one peak. When there is a large down-regulation this peak will be the internal standard from the control. In the case of gross up-regulation, this single peak will have come from the experimental sample. The problem is how to know whether a single peak is from up- or down-regulation. This is addressed by double labeling the control with $CH_3CO$—

NHS and $^{13}CH_3CO$—NHS. Because of the lysine issue noted above, it is necessary to split the control sample into two lots and label them separately with $CH_3CO$—NHS and $^{13}CH_3CO$—NHS, respectively, and then remix. When this is done the control always appears as a doublet separated by 1–2 amu, or 3 amu in the extreme case where there are two lysines in the peptide. When double labeling the control with $^{12}C$ and $^{13}C$ acetate and the experimental sample with trideuteroacetate, spectra would be interpreted as follows. A single peak in this case would be an indicator of strong up-regulation. The presence of the internal standard doublet alone would indicate strong down-regulation.

Another potential problem with the double labeled internal standard is how to interpret a doublet separated by 3 amu. Because the control sample was labeled with $CH_3CO$—NHS and $^{13}CH_3CO$—NHS, this problem can arise only when the signature peptide has 2 lysine residues and is substantially down-regulated to the point that there is little of the peptide in the experimental sample. The other feature of the doublet would be that the ratio of peak heights would be identical to the ratio in which the isotopically labeled control peptides were mixed. Thus, it may be concluded that any time a doublet appears alone in the spectrum of a sample and A is roughly equivalent to that of the internal standard that i) the two peaks came from the control sample and ii) peaks from the experimental sample are absent because of substantial down regulation.

Software Development

The isotope labeling method of the invention allows the identification of the small number of proteins (peptides) in a sample that are in regulatory flux. Observations of spectra with 50 or fewer peptides indicate that individual species generally appear in the spectra as bundles of peaks consisting of the major peptide ion followed by the $^{13}C$ isotope peaks. Once a peak bundle has been located, peak ratios within that bundle are evaluated and compared with adjacent bundles in the spectrum. Based on the isotopes used in labeling, simple rules can be articulated for the identification of up- and down-regulated peptides in mass spectra. Software can be written that apply these rules for interpretation.

Data processed in this way can be evaluated in several modes. One is to select a given peptide and then locate all other peptides that are close in δ value. All peptides from the same protein should theoretically have the same δ value (i.e., the same relative degree of up- or down-regulation). For example, when more than one protein is present in the same 2-D gel spot there is the problem of knowing which peptides came from the same protein. The δ values are very useful in this respect, and provide an additional level of selection. The same is true in 2-D chromatography. 3-D regulation maps of chromatographic retention time vs. peptide mass vs. δ can also be constructed. This identifies proteins that are strongly up- or down-regulated without regard to the total amount of protein synthesized. In some experiments, one or more groups of proteins may be identified that have similar δ values, and identification of the members of a group may elucidate metabolic pathways that had not previously been characterized.

The Internal Standard Method Applied to 2-D Gels

Advantageously, the internal standard method of the invention can be used in concert with conventional 2-D gel electrophoresis. The great advantage of 2-D electrophoresis is that it can separate several thousand proteins and provide a very good two dimensional display of a large number of proteins. The method of the invention allows this two dimensional display to be used to identify those species that are up- or down-regulated. Researchers in the past have tried to do this by comparing the staining density of proteins from different experiments (L. Anderson et al., *Electrophoresis* 17:443–453 (1997)); S. Pederson et al., *Cell* 14:179–190 (1977). However staining is not very quantitative, it is difficult to see those proteins that are present in small amounts, and multiple electrophoresis runs are required.

The detection and quantitation problems in 2-D gel electrophoresis can be solved by post-biosynthetically derivatizing proteins with either radionuclides or stable isotope labeling agents before electrophoresis to facilitate detection and quantification. The great advantage of this approach is that the labeling agents do not have to be used in the biological system. This circumvents the necessity of in vivo radiolabeling that is so objectionable in human studies with current labeling techniques. A second major advantage is that the degree of up- or down-regulation can be determined in a single analysis by using combinations of isotopes in the labeling agents, i.e., $^{14}C$ and $^3H$, $^1H$ and $^2H$, or $^{12}C$ and $^{13}C$ labels. Control samples are labeled with one isotope while experimental samples are labeled with another.

Two preferred methods were described above for labeling polypeptides post-biosynthetically: (a) labeling cysteine during alkylation and reduction of sulfhydryls and (b) labeling by acetylation of free amino groups. Labeling through reduction and alkylation of disulfides is obviously the easiest way and the most preferred for subsequent electrophoretic analysis because it does the least to disturb the charge.

Radioisotopes. Determining the ratio of radionuclides in 2-D gels requires a special detection method. The energy of β particles from $^3H$ is roughly 0.018 Mev whereas the radiation from $^{14}C$ is approximately 0.15 Mev. This difference in energy is the basis for discriminating between these two radionuclides. Counting $^3H$ requires a very thin mylar window. This fact can be exploited for differential autoradiographic detection with a commercial imager (e.g., a CYCLONE Storage Phosphor System, Packard, Meriden, Conn.). Modern imagers work by imposing a scintillator screen between the gel and the imager. Using a $^{14}C$ control and an absorption filter to block $^3H$ β radiation allows for measurement of radiation intensity for the control alone. Removing the filter and performing the autoradiographic detection again gives an intensity for $^3H+^{14}C$. Using densitometry, it is possible to determine density ratios between different spots on the same autoradiogram and between autoradiograms. The limitation of this approach is that it is difficult to recognize i) proteins that only increase slightly in concentration, ii) up- or down-regulation in a spot that contains multiple proteins, and iii) proteins that are substantially down-regulated. Down-regulation will be recognized by switching the isotopes, i.e., $^3H$ is used as the control label and $^{14}C$ as the experimental labeling agent. Once a protein spot is seen that appears to be up- or down-regulated, much better quantitation can be achieved by excising the spot and using scintillation methods for double label counting.

Phosphorylation of proteins with $^{32}P$ labeled nucleotides and glycosylation in mammalian systems with $^{14}C$ labeled N-acetylglucosamine are also envisioned, allowing studies of post-translational modifications that lend themselves to multi-isotope labeling and detection strategies.

There are several advantages of this radioisotope version of the internal standard as applied to 2-D gel electrophoresis. One is that it allows a large number of proteins to be screened for up- or down-regulation from a single sample, in a single run, with a single gel. A second is that excision of spots is not required, i.e., the degree of manual manipulation is minimal. Yet another advantage is that inter-run differences between gels and in the execution of the method have no impact on the success of the method.

Stable isotopes. Proteins that have been reduced and alkylated with either $ICH_2COOH$ or $ICD_2COOH$ and mixed before electrophoresis are used to produce peptide digests in which a portion of cysteine containing peptides are deuterium labeled. These peptides appear as doublets separated by 2 amu in the MALDI spectrum. In those cases where there are several cysteine residues in a peptide, the number of cysteines determines the difference in mass between the control and experimental samples. For each cysteine, the difference in mass increases by 2 amu. $^{13}C$ labeling can also be used. The $\Delta$ term is derived from isotope ratios in several adjacent protein spots on the gel whereas $\delta$ is computed from the ratio in the target spot. Only those peptides that deviate from the average value of $\Delta$ are targets for further analysis. This version of the internal standard method has most of the advantages of the radioisotope method in terms of quantification, use of a single sample and gel, and reproducibility. The radio- and stable-isotope strategies can also be combined and applied to 2D gel electrophoresis. The advantage of combining them is that only those spots which appear to have been up- or down-regulated by radioactive analysis are subjected to MALDI-MS. When stable and radio-labeled peptides are used in the same experiment, the stable isotopes are a way to identify and fine tune quantification.

Construction of Temporal Maps

The discussion above would imply that regulation is a process that can be understood with single measurements, i.e., after a stimulus has been applied to a biological system one makes a measurement to identify what has been regulated. Single measurements at the end of the process only identify the cast of characters. Regulation involves adjusting, directing, coordinating, and managing these characters. The issue in regulation is to understand how all these things occur. Regulation is a temporal process involving a cascade of events. Consider, for example, the hypothetical case in which an external stimulus might cause modification of a transcription factor, which then interacts with another transcription factor, the two of which initiate transcription of one or more genes, which causes translation, and finally post-translational modification to synthesize another transcription factor, etc. Temporal analysis brings a lot to understanding this process. Global analysis of protein synthesis in response to a variety of stimuli has been intensely examined and at least two mapping strategies have been developed (R. VanBogelen et al., in F. Neidhardt et al., Ed. *Escherichia coli and Salmonella: Cellular and Molecular Biology*, 2nd Ed. ASM Press, Washington D.C., pp. 2067–2117); H. Zhang et al., J. Mass Spec. 31:1039–1046 (1996)).

A temporal map of protein expression can be constructed by first identifying all species that change in response to a stimulus, then performing a detailed analysis of the regulatory process during protein flux. Identification of those proteins affected by the stimulus is most easily achieved by a single measurement after the regulatory event is complete and everything that has changed is in a new state of regulation. Both chromatographic and electrophoretic methods can be used to contribute to this level of understanding. The regulatory process during protein flux is then analyzed at short time intervals and involves many samples. The initial identification process yields information on which species are in flux, their signature peptides, and the chromatographic behavior of these peptides. As a result, the researcher thus knows which samples contain specific signature peptides and where to find them in mass spectra. Quantitating the degree to which their concentration has changed with the internal standard method is straightforward. The resulting data allows temporal maps of regulation to be constructed, and the temporal pattern of regulation will provide information about the pathway of response to the stimulus. The invention thus further provides a method for developing algorithms that identify signature peptides in regulatory change.

Microfabricated Analytical Systems

The method of the invention is amenable to automation by integrating most of the analytical steps in a single instrument. Alkylation, reduction, proteolysis, affinity selection, and reversed phase chromatography (RPC) can be executed within a single multidimensional chromatographic system. Samples collected from this system are manually transferred to MALDI plates for mass spectrometric analysis. In one embodiment, the invention provides a single channel integrated system. In a preferred embodiment, however, the invention thus provides a microfabricated, integrated, parallel processing, microfluidic system that carry out all the separation components of analysis on a single chip.

EXAMPLES

The present invention is illustrated by the following examples. It is to be understood that the particular examples, materials, amounts, and procedures are to be interpreted broadly in accordance with the scope and spirit of the invention as set forth herein Example I Signature Peptide Approach to Detecting Proteins in Complex Mixtures The objective of the work presented in this example was to test the concept that tryptic peptides may be used as analytical surrogates of the protein from which they were derived. See Geng et al., *Journal of Chromatography A*, 870 (2000) 295–313; Ji et al., *Journal of Chromatography B*, 745 (2000) 197–210. Proteins in complex mixtures were digested with trypsin and classes of peptide fragments selected by affinity chromatography (in this case, lectin columns were used). Affinity selected peptide mixtures were directly transferred to a high-resolution reversed-phase chromatography column and further resolved into fractions that were collected and subjected to matrix-assisted laser desorption ionization (MALDI) mass spectrometry. The presence of specific proteins was determined by identification of signature peptides in the mass spectra.

Advantages of this approach are that (i) it is easier to separate peptides than proteins, (ii) native structure of the protein does not have to be maintained during the analysis, (iii) structural variants do not interfere and (iv) putative proteins suggested from DNA databases can be recognized by using a signature peptide probe.

Materials and Methods

Materials. Human serotransferrin, human serum, N-tosyl-L-phenylalanine chloromethyl ketone (TPCK)-treated trypsin, concanavalin A (Con A), *Bandeiraea simplicifolia* (BS-II) lectin, tris(hydroxymethyl)aminomethane (Tris base), iodoacetic acid, tris(hydroxymethyl)aminomethane hydrochloride (Tris acid), cysteine, dithiothreitol (DTT), N-tosyl-L-lySyl chloromethyl ketone (TLCK), and N-acetyl-D-glucosamine were purchased from Sigma (St. Louis, Mo., USA). Nuclear extract from calf thymus was provided by Professor M. Bina (Department of Chemistry, Purdue University, W. Lafayette, Ind., USA). LiChrospher Si 1000 (10 μm, 1000 Å) was obtained from Merck (Darmstadt, Germany). 3,5-Dimethoxy-4-hydroxycinnamic acid (sinipinic acid), 3-aminopropyltriethoxysilane, polyacrylic acid (PAA), and dicyclohexyl carbodiimide (DCC), $d_3$-$C^1$ acetic anhydride were purchased from Aldrich (Milwaukee, Wis., USA). Methyl-α-D-mannopyranoside was obtained from Calbiochem (La Jolla, Calif., USA). Toluene, 4-dioxane and dimethylsulfoxide (DMSO) were purchased from Fisher Scientific (Fair Lawn, N.J., USA). N-Hydroxyl succinimide (NHS) and high-performance liquid chromatography (HPLC)-grade trifluoroacetic acid (TFA) were purchased from Pierce (Rockford, Ill., USA). HPLC-grade water and acetonitrile (ACN) were purchased from EM science (Gibbstown, N.J., USA). All reagents used directly without further purification.

Synthesis of lectin column. A 1-g of LiChrospher Si 1000 was activated for 5 hours at room temperature by addition of 40 ml 6 M HCl. The silica particles were then filtered and washed to neutrality with deionized water after which they were dried initially for 2 hours at 105° C. and then at 215° C. overnight. Silica particles thus treated were reacted with 0.5% 3-aminopropyltriethoxysilane in 10 ml toluene for 24 hours at 105° C. to produce 3-aminopropylsilane derivatized silica (APS silica). Polyacrylic acid (0.503 g; $M_r$ 450 000), N-hydroxysuccinamide (1.672 g), and dicyclohexyl carbodiimide (6.0 g) were dissolved into 40 ml DMSO and shaken for 3 hours at room temperature to activate the polymer. The reaction mixture was filtered and the activated polymer harvested in the supernatant. Acrylate polymer was grafted to the silica particles by adding the APS silica described above to the activated acrylate polymer containing supernatant. Following a 12-hour reaction at room temperature, the particles were filtered and washed sequentially with 50 ml DMSO, 50 ml dioxane and 50 ml deionized water. This procedure produces a polyacrylate coated silica with residual N-acyloxysuccinamide activated groups, specified as NAS-PAA silica. NAS-PAA silica (0.5 g) was added to 10 ml of 0.1 M $NaHCO_3$ (pH 7.5) containing 0.2 M methyl-α-D-mannopyranoside and 200 mg Con A. The reaction was allowed to proceed with shaking for 12 hr at room temperature after which immobilized Con A sorbent was isolated by centrifugation and was washed with 0.1 M Tris buffer (pH 7.5). The sorbent was stored in 0.1 M Tris buffer (pH 7.5) with 0.2 M NaCl until use.

NAS-PAA silica (0.3 g) was added to 10 ml of 0.1 M $NaHCO_3$ buffer (pH 7.5) containing 0.2 M N-acetyl-D-glycosamine and 20 mg BS-II lectin. The reaction was allowed to proceed with shaking for 12 hours at room temperature after which the immobilized lectin containing particles were isolated by centrifugation, washed with 0.1 M (pH 7.5) Tris buffer, and packed into a stainless steel column (50×4.6 mm) using the wash buffer and a high-pressure pump from Shandon Southern Instruments (Sewickley, Pa., USA). Affinity columns were washed by 0.1 M Tris (pH 7.5) with 0.2 M NaCl before use.

Proteolysis. Human serotransferrin (5 mg), nuclear extract from bovine cells, or human serum were reduced and alkylated in the same way by adding to 1 ml 0.2 M Tris buffer (pH 8.5) containing 8 M urea and 10 mM DTT. After a 2-h incubated at 37° C., iodoacetic acid was added to a final concentration of 20 mM and incubated in darkness on ice for a further 2 hours. Cysteine was then added to the reaction mixture to a final concentration of 40 mM and the reaction allowed to proceed at room temperature for 30 min. After dilution with 0.2 M Tris buffer to a final urea concentration of 3 M, TPCK-treated trypsin (2%, w/w, of enzyme to that of the protein) was added and incubated for 24 hours at 37° C. Digestion was stopped by adding TLCK in a slight molar excess over that of trypsin.

Chromatography. All chromatographic steps were performed using an Integral microanalytical workstation from PE Biosystems (Framingham, Mass., USA). Tryptic digested human serotransferrin (0.1 ml) was injected onto the Con A affinity column that had been equilibrated with a loading buffer containing 1 mM $CaCl_2$, 1 mM $MgCl_2$, 0.2 M NaCl and 0.1 M Tris-HCl (pH 7.5). The Con A column was eluted sequentially at 1 ml/min with two column volumes of loading buffer and then 0.2 M methyl-α-D-mannopyranoside in 0.1 M Tris (pH 6.0). Analytes displaced from the affinity column with 0.2 M methyl-α-D-mannopyranoside were directed to a 250×4.6 mm Peptide $C_{18}$ (PE Biosystems) analytical reversed-phase HPLC column, which had been equilibrated for 5 minutes at 1.0 ml/min with 5% ACN containing 0.1% aqueous TFA. The glycopeptides were then eluted at 1.0 ml/min in a 35-min linear gradient to 50% ACN in 0.1% aqueous TFA. Eluted peptides were monitored at 220 nm and fractions manually collected for matrix-assisted laser desorption ionization time-of-flight (MALDI-TOF) analysis.

Tryptic digested human serum (0.2 ml) was injected on the Con A and reversed-phase HPLC column using conditions similar to those used with human serotransferrin with the following exceptions. The reversed-phase column was washed for 10 minutes at 1 ml/min with 10% ACN containing 0.1% aqueous TFA and the glycopeptides were eluted at 1 ml/min with a 120-min linear gradient to 70% ACN containing 0.1% aqueous TFA.

Nuclear extract (0.1 ml) was injected onto the BS-II column which had been equilibrated with loading buffer, 0.2 M NaCl with 0.1 M Tris (pH 7.5). After sample loading the BS-II column was washed with 20 column volumes of loading buffer and then eluted with 0.2 M N-acetyl-D-glyCosamine in the loading buffer. Glycopeptides and glycoproteins eluted from the BS-II column were transferred to a reversed-phase column, which had been equilibrated for 5 minutes at 1 ml/min with 5% ACN containing 0.1% aqueous TFA. The glycoproteins were then eluted at 1 ml/min with a 25-min linear gradient to 35% ACN containing 0.1% aqueous TFA. The glycopeptides were eluted at 1 ml/min with a 35-min linear gradient to 50% ACN containing 0.1% aqueous TFA.

Synthesis of $d_3$-$C^1$ N-acetoxysuccinamide[1]. A solution of 4.0 g (34.8 mmol) of N-hydroxysuccinimide in 10.7 g (105 mmol) of $d_3$-$C^1$ acetic anhydride was stirred at room temperature. After 10 minutes, white crystals began to deposit. The liquid phase was allowed to evaporate and the crystalline residue extracted with hexane which is allowed to dry in vacuum. The yield of the substances was 5.43 g (100%), m.p. 133–134° C.

Acetylation reaction with the peptides. A 3-fold molar excess of N-acetoxysuccinamide and $d_3$-$C^1$ N-acetoxysuccinamide was added individually to the two equal aliquots of 1 mg/ml peptide solution in phosphate buffer at pH 7.5, respectively. The reaction was carried at room temperature. After stirring for about 4–5 hours, equal aliquots of the two samples were mixed and purified on a $C_{18}$ column. The collected fraction were then subjected to MALDI-MS.

MALDI-TOF-MS. MALDI-TOF-MS was performed using a Voyager DE-RP BioSpectrometry workstation (PE Biosystems). Samples were prepared by mixing a 1-μl aliquot with 1 µl of matrix solution. The matrix solution for glycopeptides was prepared by saturating a water-ACN (50:50, v/v), 3% TFA solution with sinipinic acid. A 1-µl sample volume was spotted into a well of the MALDI sample plate and allowed to air-dry before being placed in the mass spectrometer. All peptides were analyzed in the linear, positive ion mode by delayed extraction using an accelerating voltage of 20 kV unless otherwise noted. External calibration was achieved using a standard "calibration 2" mixture from PE Biosystems.

The matrix for acetylated peptides was a solution of 3% TFA, ACN-water (50:50) solution saturated with a α-cyano-4-hydroxycinnamic acid. Peptide quantitation was performed on MALDI-TOF-MS in the reflector mode as described above. Ten spectra were collected from each sample spot and the peak intensities averaged for each spot. A linear equation was deduced from the ion current intensity ratio of the deuterium-labeled and the unlabeled acetylated peptides versus the ratio of the amount of these two peptides.

The effect of buffer type and concentration on mass determination by MALDI-time-of-flight mass spectrometry is discussed in Amini et al., *Journal of Chromatography A*, 894 (2000) 345–355.

Results and Discussion

Analytical strategy. The work reported here is based on the proposition that signature peptides generated by tryptic digestion of sample proteins may be selected from complex mixtures and be used as analytical surrogates for the protein from which they were derived. The rationale for this approach is that (i) it will be easier to separate and identify signature peptides than intact proteins in many cases, (ii) the requisite isolation of proteins for reagent preparation and identification can be precluded by synthesizing signature peptides identified in protein and DNA databases, and (iii) it is easier to tryptic digest all proteins in a single reaction than to isolate and digest each individually as in the 2D electrophoretic approach.

A five-step protocol was used for production of signature peptides. The first step was to select a sample from a particular compartment of organelle. Simple methods, such as centrifugal fractionation of organelles, greatly enrich a sample in the components being examined. The second step embodied reduction and alkylation of all proteins in the sample. In some cases the alkylating agent can be affinity labeled to facilitate subsequent selection of cysteine-containing peptides. The third step was tryptic digestion of all polypeptides in the reduced and alkylated sample. A few to more than a hundred peptides will be generated from each protein, depending on solubility and ease of digestion. Although data are not presented, it was found that trypsin will partially digest leather and by so doing generates signature peptides. This potentially offers an avenue to the analysis of insoluble proteins. The enormous complexity of the sample produced by proteolysis was reduced in a third step by using affinity chromatography methods to select peptides with unique structural features. Affinity selected peptides were then fractionated by high-resolution RPLC in a fourth step. And finally, target peptides from RPLC fractions were identified by MALDI-TOF-MS mass in the fifth step.

The analytical strategy employed in this study focused on the ability of Con A lectin columns to select glycopeptides from tryptic digests, RPLC to further fractionate the selected peptides, and MALDI-TOF-MS to identify specific peptides in RPLC fractions. Lectin columns have been widely used to purify glycopeptides, generally for the purpose of studying the oligosaccharide portion of the conjugate. When characterization of the sugar moiety is the object, it is important to fractionate as many of the glycoforms as possible, either with serial lectin columns, anion-exchange chromatography, or capillary electrophoresis. The focus of this work, in contrast, was on the peptide portion of the glycoconjugate. Any glycoform containing the signature peptide backbone is appropriate for protein identification. Con A has high affinity for N-type hybrid and high-mannose oligosaccharides, slightly lower affinity for complex di-antenary oligosaccharides, and virtually no affinity for complex N-type tri- and tetra-antenary oligosaccharides. Most of the N-type glycoproteins contain glycoforms that are recognized by Con A. Thus, a Con A column is ideal for selecting glycopeptides from digests of N-type glycoproteins.

Compartmentalization. Protein(s) of interest often residue in a particular compartment in a cell or organism. The act of first isolating the compartment within which the protein is contained can produce a very substantial simplification of the sample. One system chosen for this study was glycoproteins in bovine cellular nuclei.

Glycoproteins in the nuclei of mammalian cells are uniquely different to those found in the cytosol. Higher animal cells reversibly O-glycosylate some nuclear proteins with a single N-acetyl glucosamine (O-GlcNAc) at a specific serine or threonine residue. It is thought that this O-GlcNAc glycosylation is associated with transcription factors and is part of a control process; thus it is necessary to have enzymes for both glycosylate and deglycosylate in the same compartment. It was an objective in this study to gain a rough idea of the number of these glycoproteins in the nuclei of bovine pancreas cells.

Subsequent to the isolation of nuclei by centrifugation, histones were selectively removed and O-glycosylated proteins isolated as a group by chromatography on a *Bandeiraea simplicifolia* (BS-II) lectin affinity column. This lectin is specific for N-acetyl glucosamine. A silica based BS-II column was synthesized and coupled with a switching valve to a reversed-phase column. This two-dimensional chromatographic system was used to concentrate and purify glycoproteins from nuclei. Reversed-phase chromatography (FIG. 2) and 2D gel electrophoresis of the protein fraction eluted from the lectin column by N-acetyl-D-glucosamine (0.20 M) confirm the presence of some 25–35 major components in the sample. More components may be present but below the limits of detection. Considering that some 20,000 proteins may be expressed in mammalian cells, this is much simpler than anticipated. The results of this study show that compartmentalization and affinity selection of specific proteins from a cell can greatly reduce the number of proteins in a sample.

Figure 3:
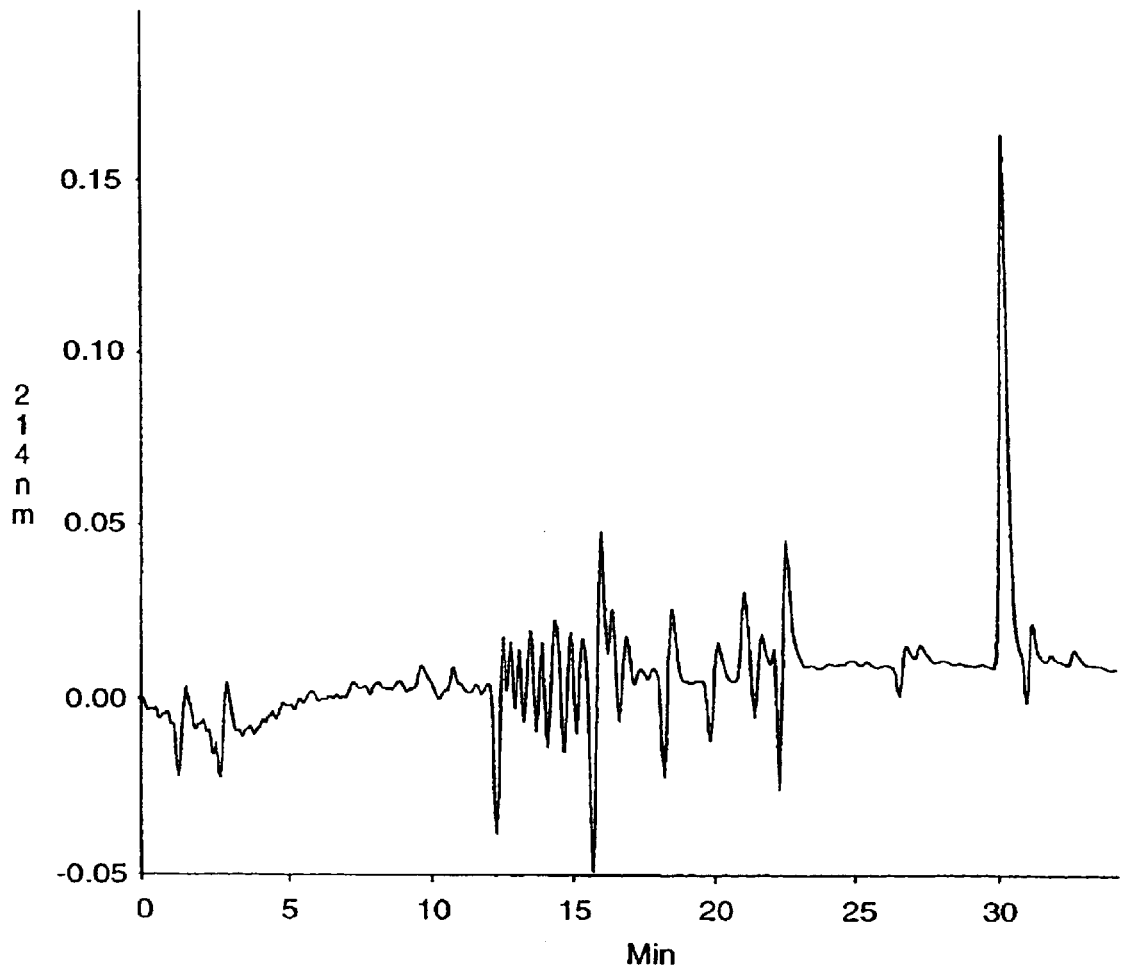
FIG. 3 is a reversed-phase chromatogram of tryptic digested glycopeptides isolated from bovine nuclei by chromatography on a BS-II lectin affinity column. Elution was achieved using a 0.20 M solution of N-acetylglucosamine.
Figure 4A:
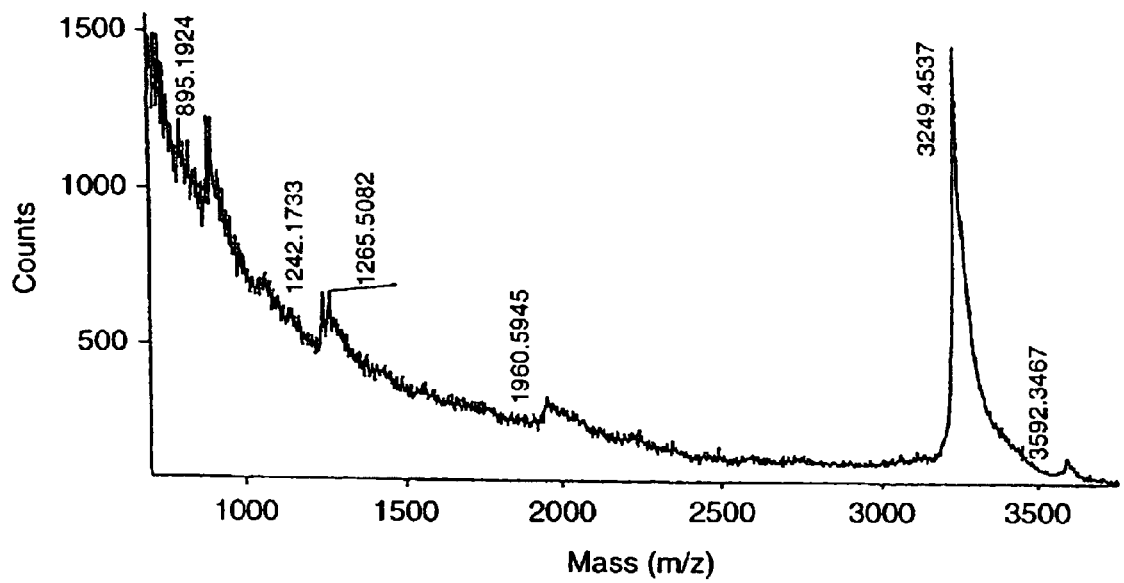
FIGS. 4(*a*)–(*d*) shows mass spectra of various glycopeptide fractions collected from the reversed phase column.
Figure 4B:
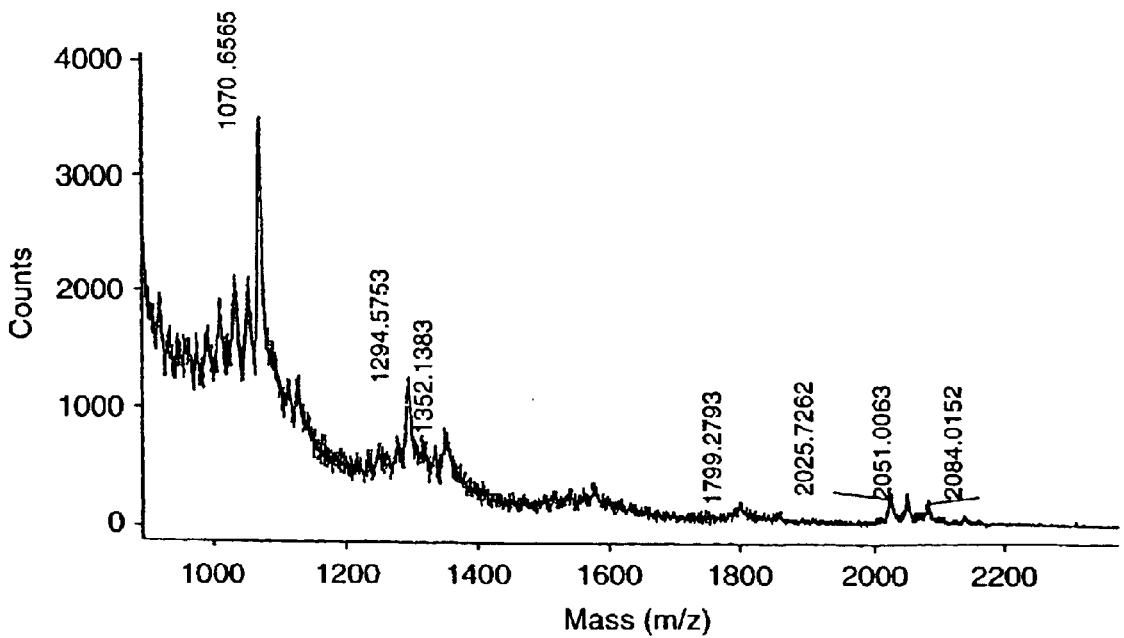
Figure 4C:
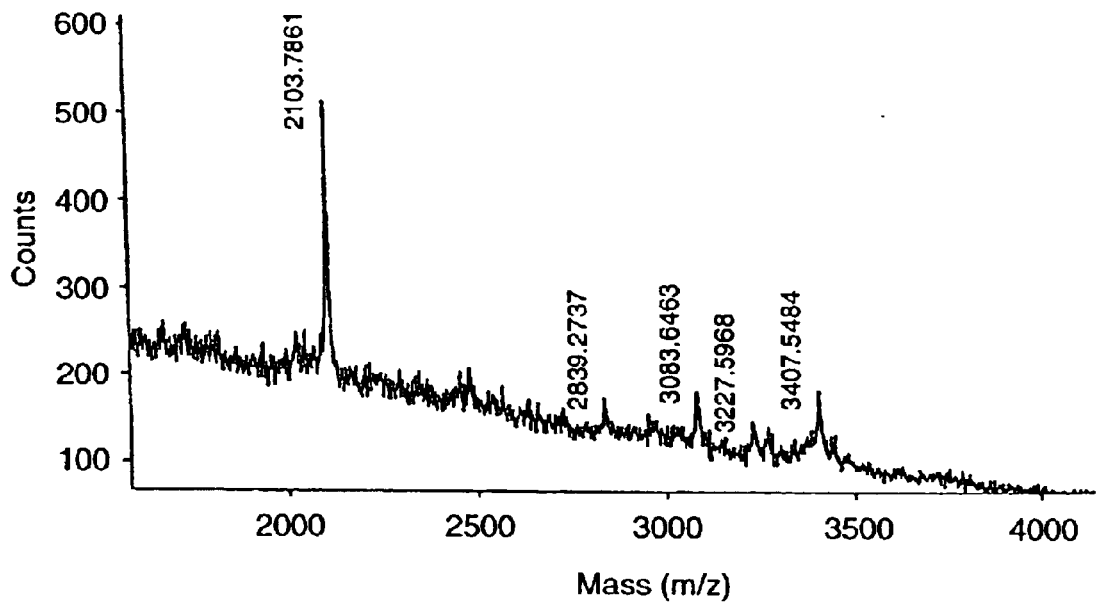
Figure 4D:
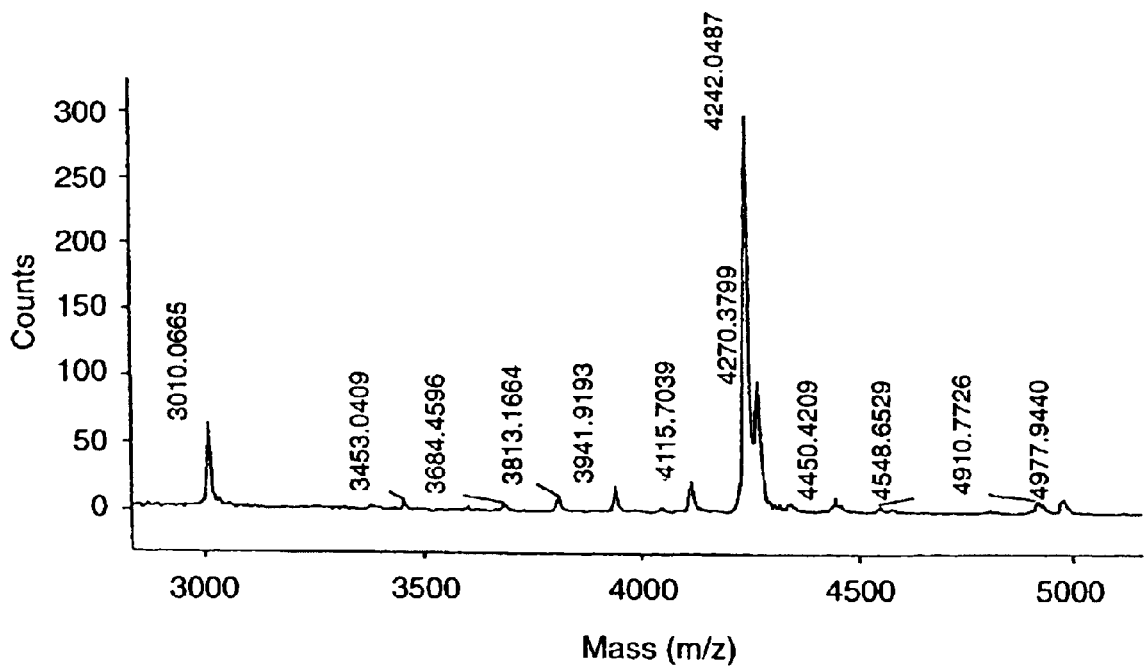

When the protein sample used for glycoprotein analysis was reduced, alkylated with iodoacetamide, and trypsin digested before chromatography on the (BS-II) lectin affinity column, the reversed-phase chromatogram of the glycopeptides captured by the affinity column again shows unexpected simplicity (FIG. 3). Mass spectra of selected peaks (FIG. 4) indicate a relatively low degree of complexity in fractions collected from the reversed-phase column. No attempt was made to identify these peptides by either database searches or multidimensional MS.

Figure 5A:
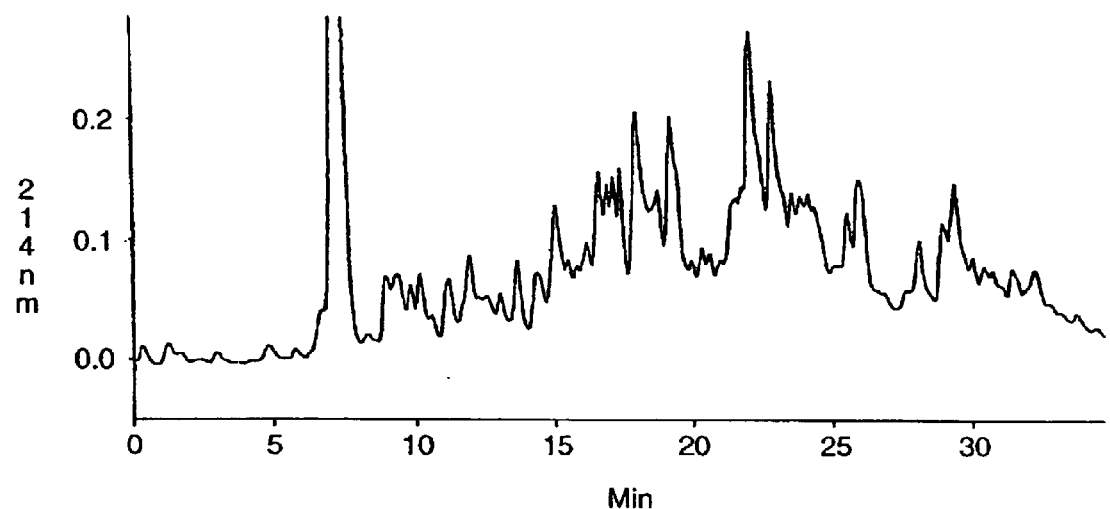
FIG. 5 is a reversed-phase chromatogram of (a) a peptide map of human serotransferrin and (b) two human serotransferrin glycopeptides isolated from a conconavalin A column.
Figure 5B:
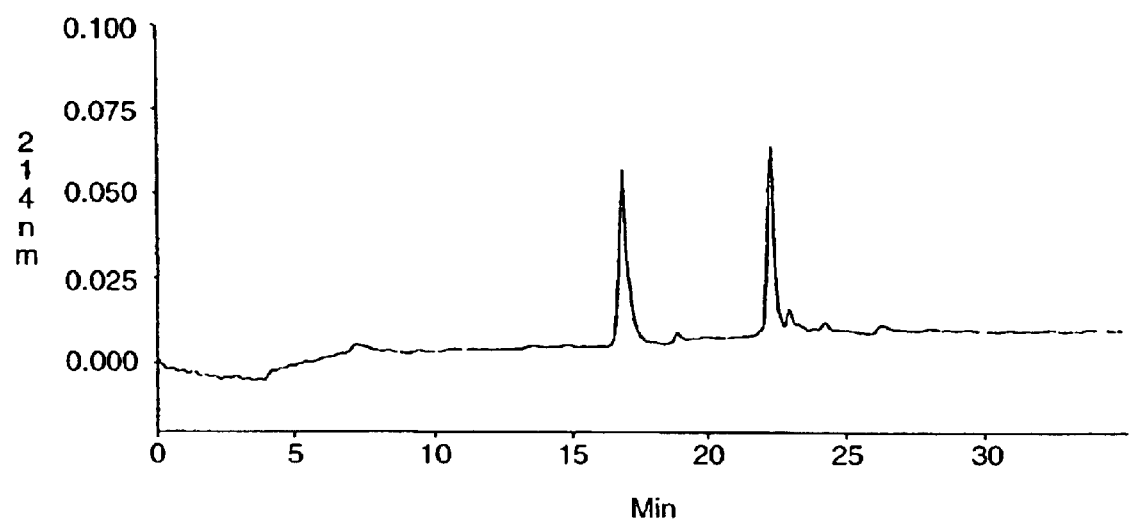
Figure 6A:
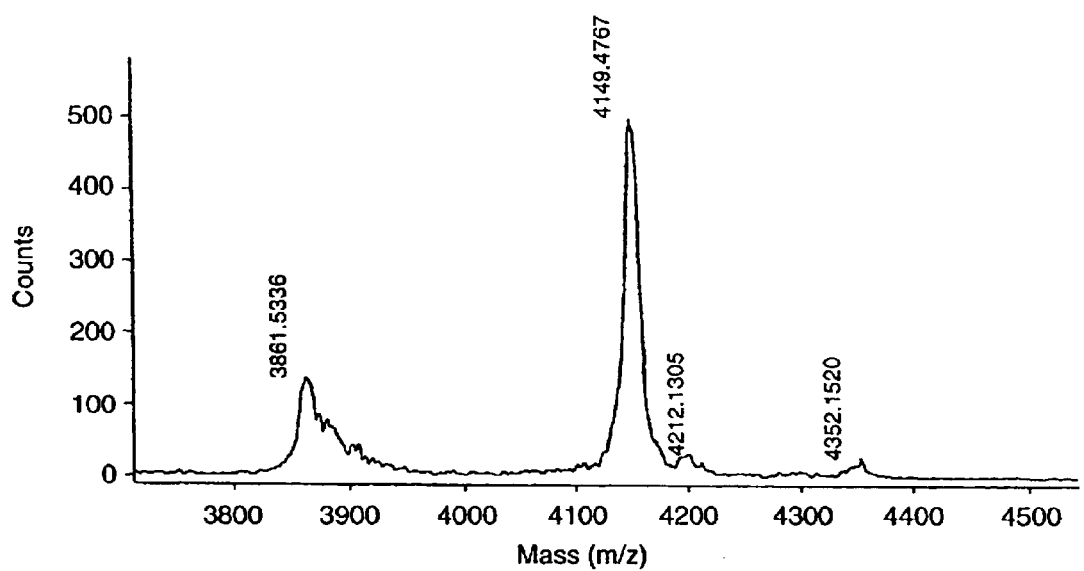
FIG. 6 is a matrix-assisted laser desorption ionization-time of flight (MALDI-TOF mass spectrum of (a) the first glycopeptide from human serotransferrin and (b) the second glycopeptide from human serotransferrin.
Figure 6B:
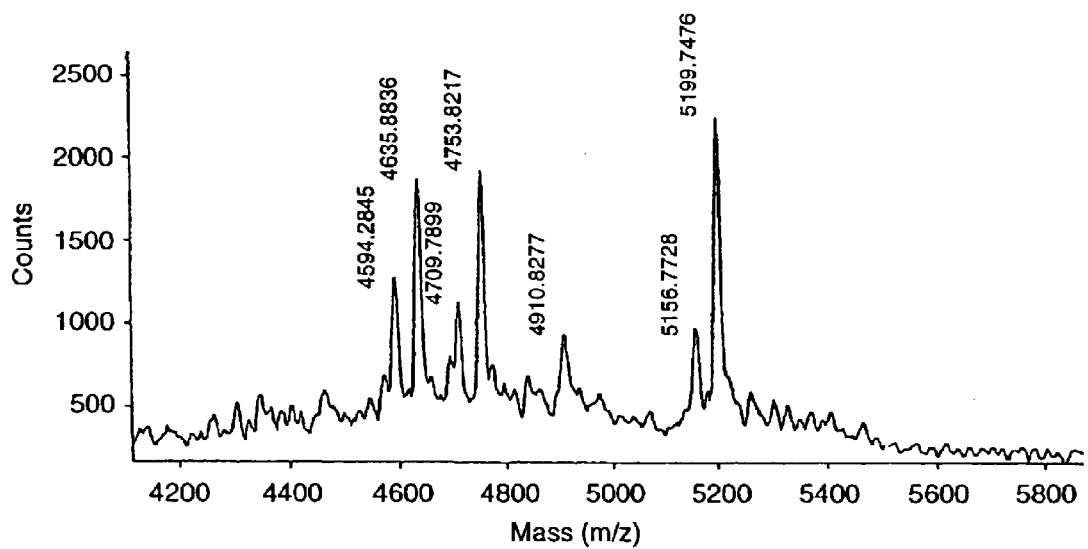

Signature peptide selection from serotransferrin. Serotransferrin, i.e., transferrin from serum, was chosen as a model protein to examine affinity selection of affinity peptides. Human serotransferrin is a glycoprotein of $M_r$ 80,000 containing 679 amino acid residues. Potential sites for N-glycosylation are found in the sequence at residues $Asn_{413}$ and $Asn_{611}$. The reversed-phase chromatogram of a tryptic digest (FIG. 5a) is seen to be substantially reduced in complexity when non-glycosylated peptides are first removed with a concanavalin A affinity chromatography column (FIG. 5b). The peptides glycosylated at residues $Asn_{413}$ and $Asn_{611}$ eluted at 27.5 and 33.4% of solvent B, respectively. MALDI-MS of the two major components from FIG. 6b are seen in FIGS. 6a and 6b, respectively. Although the chromatographic peaks appear to be homogenous, MALDI-TOF-MS indicates considerable heterogeneity within the two fractions. This is as expected. It is known that there is often substantial heterogeneity in the oligosaccharide portion of a glycopeptide. The stationary phase of the reversed-phase column interacts almost exclusively with the peptide region of glycopeptides, essentially ignoring the oligosaccharide portion. This means that glycopeptides which are polymorphic in the oligosaccharide part of the molecule will produce a single chromatographic peak, albeit slightly broader than that of a single species. On the other hand, MALDI-TOF-MS discriminates on the basis of mass and detects all species that differ in mass without regard to structure. Used together, these two methods produce a high degree of structural selectivity.

Figure 7A:
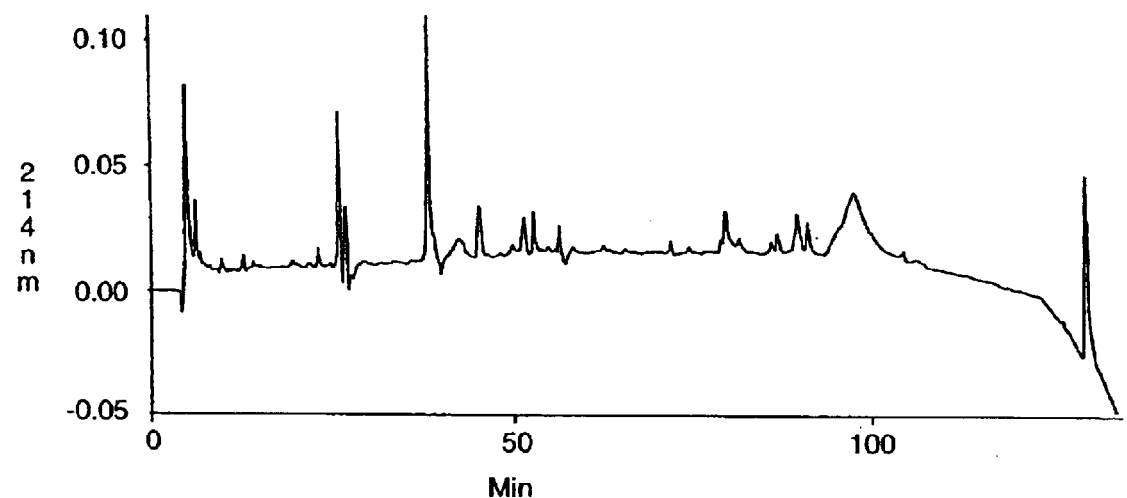
FIG. 7 is a reversed-phase chromatogram of (a) glycopeptides isolated from human serum and (b) glycopeptides isolated from human serum.
Figure 7B:
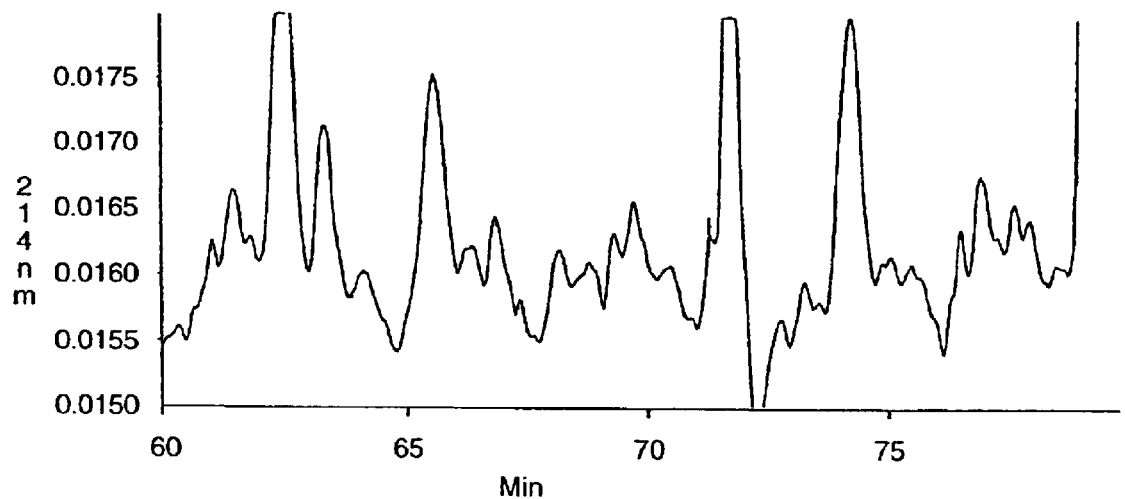
Figure 8A:
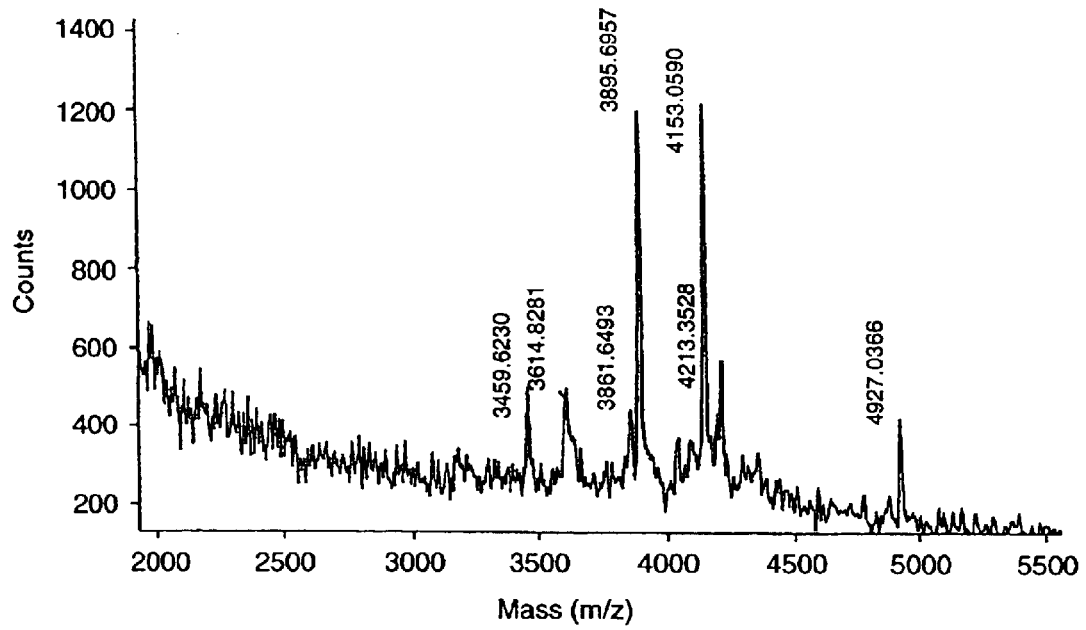
FIG. 8 is a mass spectrum of fractions isolated from human serum containing (a) the first glycopeptide from human serotransferrin and (b) the second glycopeptide from human serotransferrin.
Figure 8B:
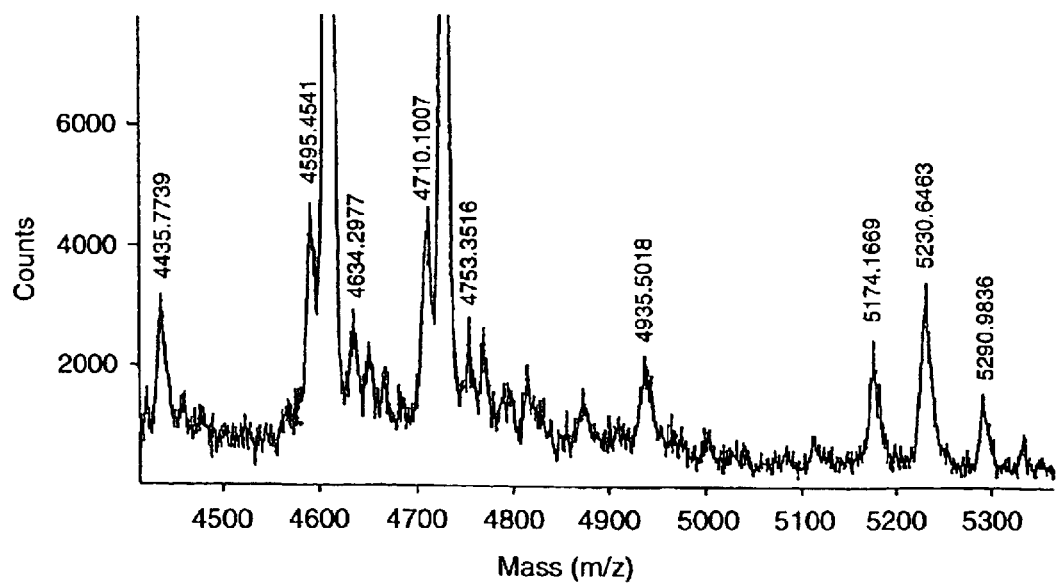

Identification of serotransferrin signature peptides from serum. Based on the solvent composition known to elute the serotransferrin glycopeptides and their mass spectra, an experiment was undertaken to identify these signature peptides in a tryptic digest of human serum proteins. Chromatograms in FIGS. 7a and 7b show the enormous complexity of the glycopeptide mixture selected from a tryptic digest of human serum by a Con A affinity chromatography column. Fractions eluting between 27 and 28% and between 33 and 34% were collected from the reversed-phase column and their mass spectra compared with that of human serotransferrin. Although extremely complex, mass spectra (FIGS. 6a and 6b) obtained from fractions corresponding in chromatographic properties to the serotransferrin glycopeptides reveal the presence of these signature peptides in the serum sample. FIG. 8a shows masses at 3861, 4163 and 4213 u, matching the glycopeptide peaks from FIG. 6a. Mass error was typically <4 u using external calibration. Because of the relatively lower amount of the human transferrin in an individual's serum, higher laser power was used to generate the spectra than that in pure human transferrin. Therefore, peak intensity were lower and spectral resolution were lower. In order to increase signal to noise ratio, all the spectra were smoothed by a 19-point averaging process. This caused the mass error to be a little higher. Glycoforms at 3459, 3614 and 3895 u were either absent or ion suppressed sufficiently so that they could not be seen. We also checked the fraction from 25 to 27% and from 29 to 31%, there was no more than one peak matching glycopeptide peaks from FIG. 6a. It demonstrated that the matching of these peaks were not coincident. FIG. 8b shows that 4595, 4634, 4710 and 4753 matched the glycopeptides peaks from FIG. 6b. Again, fractions from 31 to 33% and 34 to 36% were checked and no matching was found. The fact that the spectra are not identical in relative intensities to the standards can be explained by possible reasons: differences in glycosylation ratio between the reference protein and that in the serum sample of an individual; inter-run variations in MALDI spectra resulting from difference in MALDI ionization.

Although not examined, other modes of selection are also potentially possible. A variety of lectins are available that allow the selection of specific types of post-translational modification on the basis of oligosaccharide structure. Antibodies would be another way to select for specific types of post-translational modification such as phosphorylation. Antibodies have also been used to select dinitrophenyl derivatized amino acids, such as tryptophan. Alkylation of cysteine with a biotinylated form of maleimide has been suggested as another way to select cysteine-containing peptides with avidin. Perhaps double selection by a combination of these affinity methods will give even higher degrees of selectivity.

It is concluded that signature peptides derived from tryptic digests of complex protein mixtures can be used as analytical surrogates, at least in the case of glycoproteins. Even in the case of samples with the complexity of human serun, the multidimensional analytical approach of affinity chromatography, reversed-phase chromatography and mass spectrometry has sufficient resolution to identify single signature peptide species. Because the whole protein is not needed for analysis, this strategy is particularly suited to the identification of proteins of limited solubility or that are suggested from DNA data bases but have never been isolated.

Example II

Sample Protocol for Analysis of Protein Mixtures

The following protocol is one of many according to the invention that are useful for analyzing complex protein mixtures.

Step 1. Reduction of entire sample containing several thousand proteins in a robotic sample handling system.

Step 2. Alkylate sulfhydryl groups. If cysteine selection is desired the alkylating reagent is an affinity tagged maleimide. If the selection will be for another amino acid, the alkylating agent will be iodoacetic acid or iodoacetamide.

Step 2'. If another amino acid is to be affinity selected, such as tyrosine, that derivatizing agent is added at this time.

Step 3. Proteolysis; generally with trypsin, but any proteolytic enzyme or combination of enzymes could be used. Enzymatic digest could either be done in the robotic system or with an immobilized enzyme column.

Step 4. An affinity sorbent is used to adsorb affinity tagged species. Non-tagged peptide species are eluted to waste.

Step 5. Tagged species are desorbed from the affinity sorbent.

Step 6. Tagged species are chromatographically resolved. In the simplest case the sample is subjected to high resolution reverse phase chromatography (RPC) only. Still higher resolution can be achieved by using two dimensional chromatography. Step gradient elution ion exchange chromatography with RPC of each fraction is a good choice. Given that the ion exchange column could split the tagged species into 50 fractions and the RPC column had a peak capacity of 200, it is possible to generate 10,000 fractions for MALDI. It is estimated that the total number of sulfhydryl containing peptides would not exceed 20,000. This would mean that no sample would contain more than 2–10 peptides. MALDI should be very capable of handling 1–30 peptides per sample.

Step 7. Samples are collected from the chromatographic system and transferred directly to the MALDI plates. Alternatively, if the sample is not too complex, analytes are electrosprayed directly into an ESI-MS.

Example III

Representative Amino Acid Derivatizations

1. Tryptophan can be derivatized with 2,4-dinitrophenylsulfenyl chloride. (Biochem. Biophys. Acta. 278, 1 (1972)]. Reaction conditions: 50% acetic acid, 1 hour, room temperature. Selection is based on dinitrophenyl-directed antibodies.

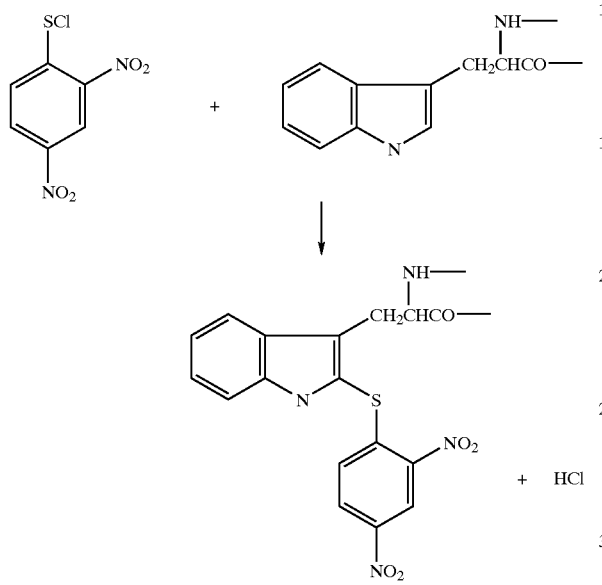

2. Cysteine can derivatized with an affinity tagged maleimide. Normal and deuterium labeled tags are mixed so that tagged species are easily identified in the MALDI spectrum as a doublet that is three mass units apart.

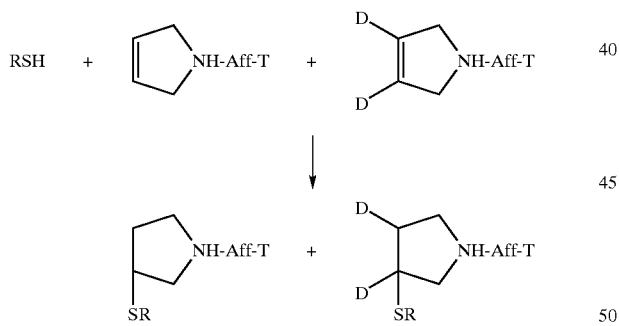

For example, cysteine residue in a polypeptide can be derivatized with affinity tagged $D_2$-maleimide. Here, the affinity tag is peptide $R_5$–$R_7$.

3. Cysteine can alternatively derivatized with 2,4-dinitrobenzyl chloride. Conditions: pH 5, 1 hour, room temperature.

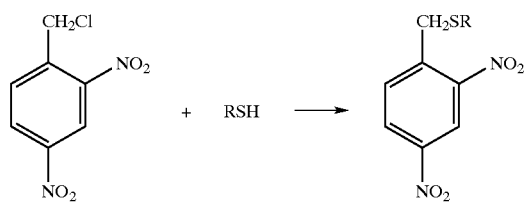

4. Methionine can be derivatized under acidic conditions. This derivatizing agent also derivatizes histidine at pH 5. The substantial ionization of histidine at pH 3 apparently diminishes its alkylation. In view of the fact that histidine reacts with this reagent, it is preferable to remove histidine peptides with IMAC before derivatization.

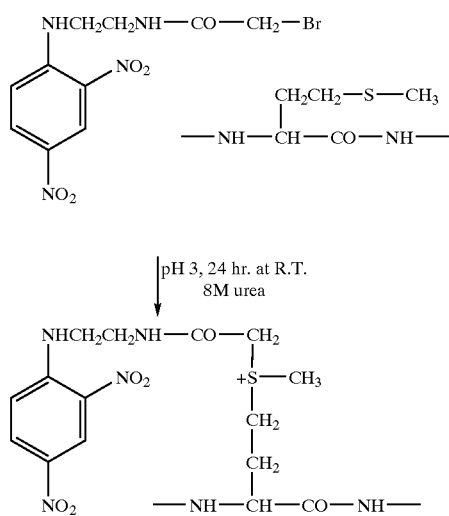

Example IV

Advantages and Disadvantages of Selective Capture of Specific Amino Acids

1. Cysteine
   a. Biotinylation of maleimide.
      Positives—very high affinity capture. Avidin columns are readily available.
      Negatives—it takes very acidic conditions to release from columns. A large molecule (avidin) is being used to capture a small molecule, thus a large column is needed to capture enough peptide for analysis.

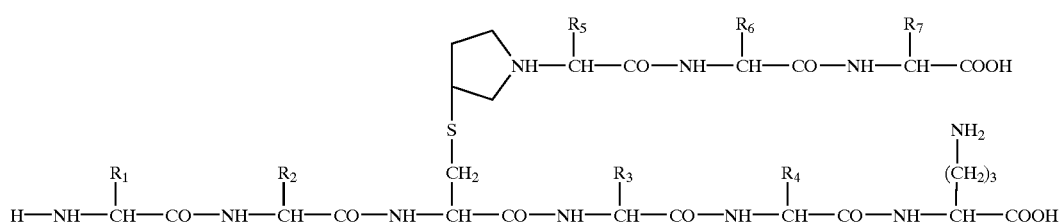

b. Histidine labeling of maleimide.
   Positives—very simple columns may be used that are of high capacity.
   Negatives—non-cysteine containing peptides in the digest that also contain histidine will also be selected. In addition, the mass starts to get a little high.
c. Peptide labeling and antibody (Ab) capture.
   Positives—very high capture efficiency. Easy to release captured peptide.
   Negatives—a large molecule (Ab) is being used to capture a small molecule, thus a large and expensive column is needed to capture enough peptide for analysis.
d. Dinitrophenylation.
   Positives—very simple organic chemistry. Antibody capture is very efficient.
   Negatives—a large molecule (Ab) is being used to capture a small molecule, thus a large and expensive colum is needed to capture enough peptide for analysis. It is also difficult to heavy isotope label 2,4-DNP.
2. Tryptophan.
   a. Dinitrophenylation.
      Positives—very simple organic chemistry. Antibody capture is very efficient.
      Negatives—a large molecule (Ab) is being used to capture a small molecule, thus a large and expensive column is needed to capture enough peptide for analysis. It is also difficult to heavy isotope label 2,4-DNP.
3. Methionine.
   a. Dinitrophenylation.
      Positives—very simple organic chemistry. Antibody capture is very efficient.
      Negatives—a large molecule (Ab) is being used to capture a small molecule, thus a large and expensive column will be needed to capture enough peptide for analysis. It is also difficult to heavy isotope label 2,4-DNP.

b. Histidine labeling.
      Positives—very simple columns may be used that are of high capacity.
      Negatives—non-cysteine containing peptides in the digest that also contain histidine will also be selected. In addition, the mass starts to get a little high.
   c. Peptide labeling and antibody capture.
      Positives—very high capture efficiency. Easy to release captured peptide.
      Negatives—a large molecule (Ab) is being used to capture a small molecule, thus a large and expensive column is needed to capture enough peptide for analysis.
   d. Biotinylation.
      Positives—very high affinity capture. Avidin columns are readily available.
      Negatives—it takes very acidic conditions to release from columns. A large molecule (avidin) is being used to capture a small molecule, thus a large column is needed to obtain enough peptide for analysis.
4. Tyrosine.
   a. Nitrophenylation and antibody capture.
      Positives—very simple organic chemistry. Antibody capture is very efficient.
      Negatives—a large molecule (Ab) is being used to capture a small molecule, thus a large and expensive column is needed to capture enough peptide for analysis. It is also difficult to heavy isotope label NP.
   b. Reaction with diazonium salts to form wide variety of derivatives.
      Positives—simple reaction that is well known.
      Negatives—very hydrophobic group, affinity tag must be attached, cross reacts with other amino acids.
5. Histidine.
   a. Capture with an IMAC column.

Example V

Sample Post-Digestion Secondary Labeling Protocol

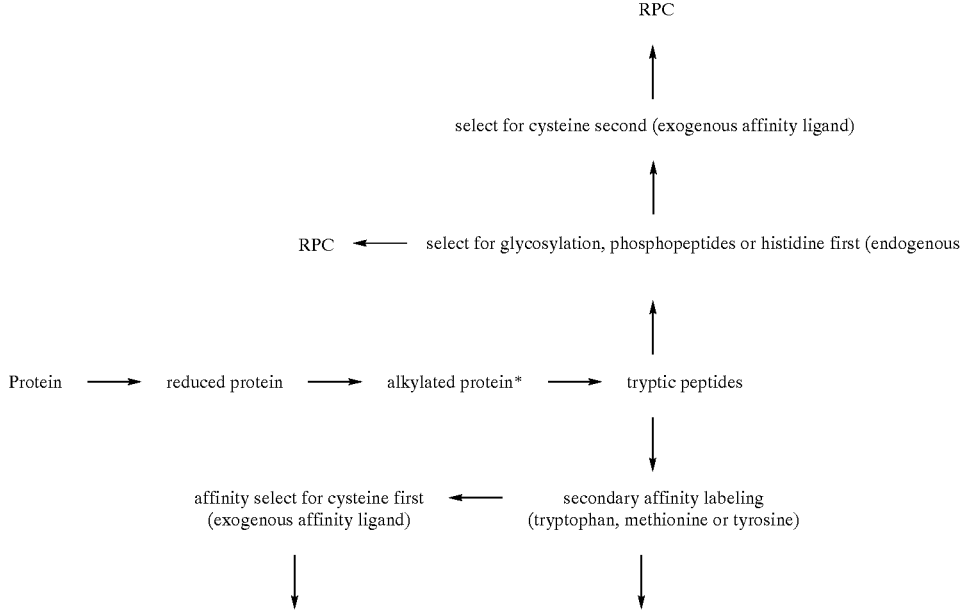

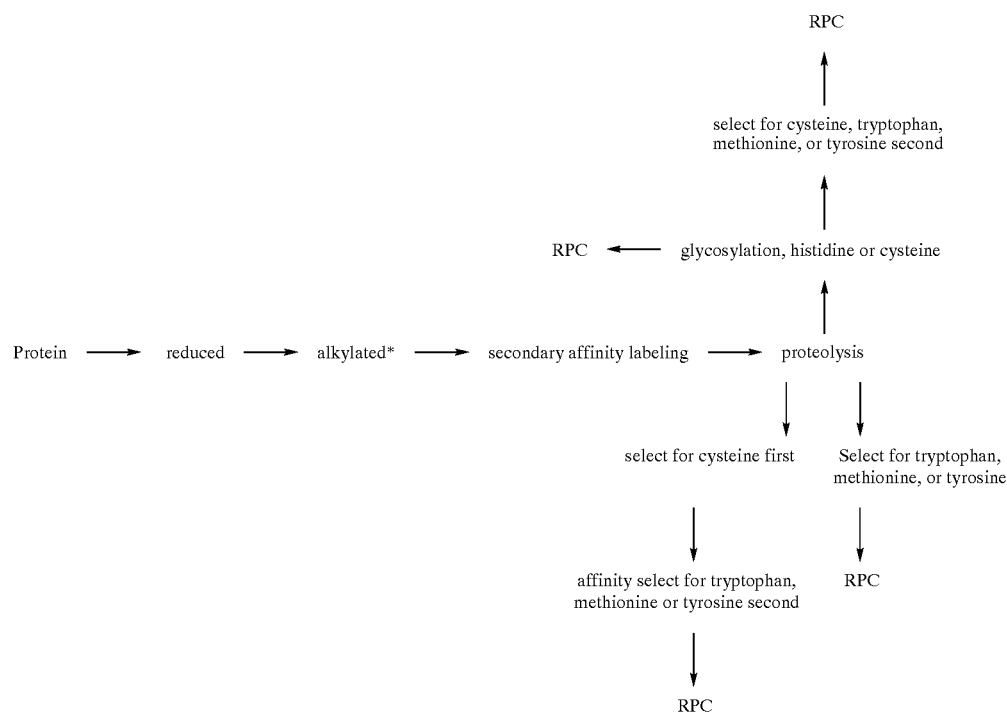

*Affinity labeling cysteine residues is optional. It should be noted, however, that cysteine must be alkylated at this point and if it is not affinity labeled during reduction, it can never be labeled.

Example VI

Sample Pre-Digestion Labeling Protocol

*Affinity labeling cysteine residues in this case is optional. It should be noted, however, that cysteine must be alkylated at this point and if it is not affinity labeled during reduction it can never be labeled.

Example VII

Isotopically Labeled Internal Standard Quantification

One of the issues with the signature peptide approach is how to quantitate the protein being identified. Because tryptic digests of samples containing many proteins are enormously complex, the mixture generally will not be resolved into individual components by reversed-phase chromatography. Simple absorbance monitoring is precluded. This will even be true with affinity selected samples as was seen in FIGS. 3 and 7. FIGS. 7a and 7b shows that there can be so many components in reversed-phase chromatograms of affinity selected samples that quantification of any particular peptide is impossible. The next avenue to quantification would be to use peak height in the MALDI-TOF spectrum. Unfortunately, MALDI-TOF is not very quantitative. A better method is needed.

Internal standards are frequently used in quantitation. The internal standard method of quantification is based on the concept that the concentration of an analyte in a complex mixture of substances may be determined by adding a known amount of a very similar, but distinguishable substance to the solution and determining the concentration of analyte relative to a known concentration of the internal standard. Assuming that the relative molar response of the detection system for these two substances ($\Re/R$) can be determined, then $A=\Lambda[\Re/R]\Delta$. The term A is the instrument response to analyte, $\Lambda$ is instrument response to the internal standard, R is specific molar response to analyte, $\Re$ is specific molar response to the internal standard, and $\Delta$ is the relative concentration of analyte to that of the internal standard. It is important that these substances are as similar as possible in chemical properties so they will behave the same way in all the steps of the analysis. In view of the fact that the last step of the analytical protocol used to identify signature peptides is MS, isotopic labeling of either the internal standard or the analyte would be the best way to produce an internal standard. Chromatographic systems are generally not able to resolve isotopic forms of an analyte whereas isotopically labeled species are easily resolved by MS. Behavioral equivalency in all stages except MS is critical. The question is how to easily create isotopically labeled internal standards of peptides in mixtures.

This may be done in two ways. One is through the synthesis of peptides in which one of the amino acids is labeled. The second is by derivatizing peptides with an isotopically labeled reagent. Although it is more lengthy, the second route was chosen because it can also be used to create internal standards of unknown structures. This is critical in proteomic studies where the object is to identify unknown proteins in regulatory flux.

Data are presented that suggest proteins may indeed be quantified as their signature peptides by using isotopically labeled internal standards. Signature peptides generated by trypsin digestion have a primary amino group pat their amino-terminus in all cases except those in which the peptide originated from the blocked amino-terminus of a protein. The specificity of trypsin cleavage dictates that the C-terminus of signature peptides will have either a lysine or arginine (except the C-terminal peptide from the protein) and that in rare cases there may also be a lysine or arginine adjacent to the C-terminus. Primary amino groups of peptides were acylated with N-hydroxysuccinimide.

Figure 9:
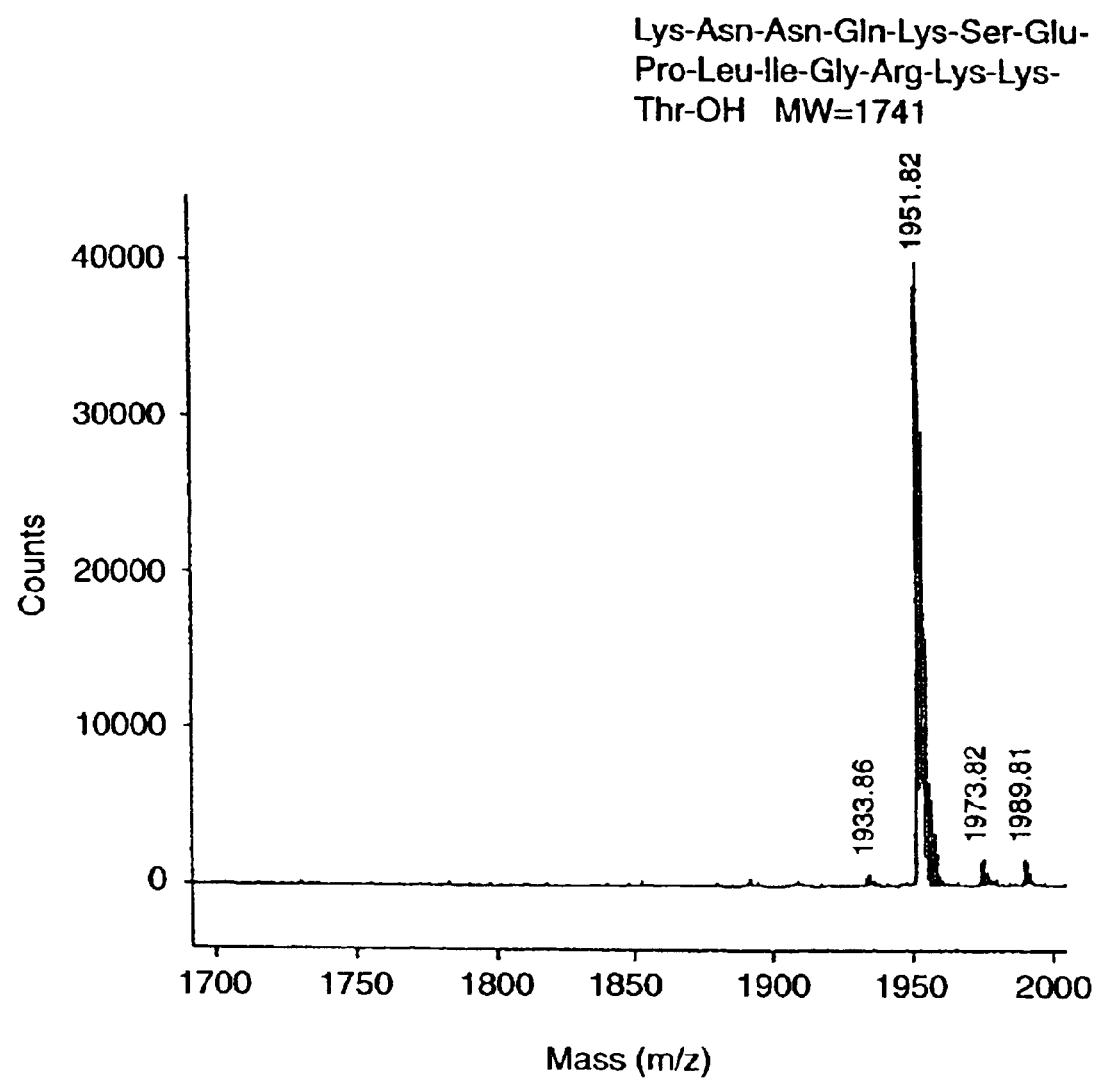
FIG. 9 is a MALDI-mass spectrum of a deuterium labeled peptide containing four lysines.
Figure 10B:
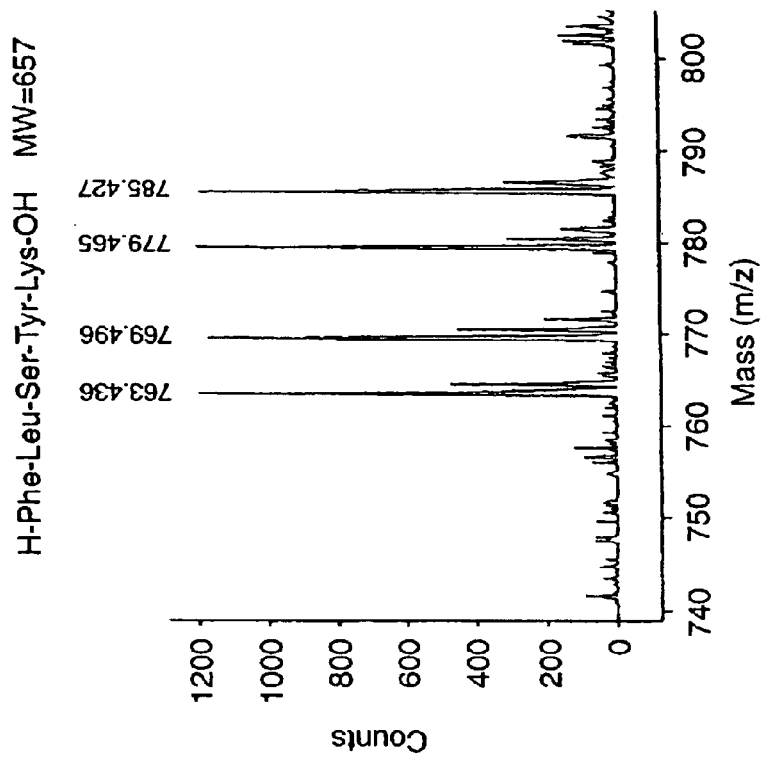
FIG. 10 is a MALDI-TOF mass spectrum of (a) labeled and unlabeled lysine-containing peptide in negative mode detection and (b) a lysine-containing peptide detected in positive mode.
Figure 10A:
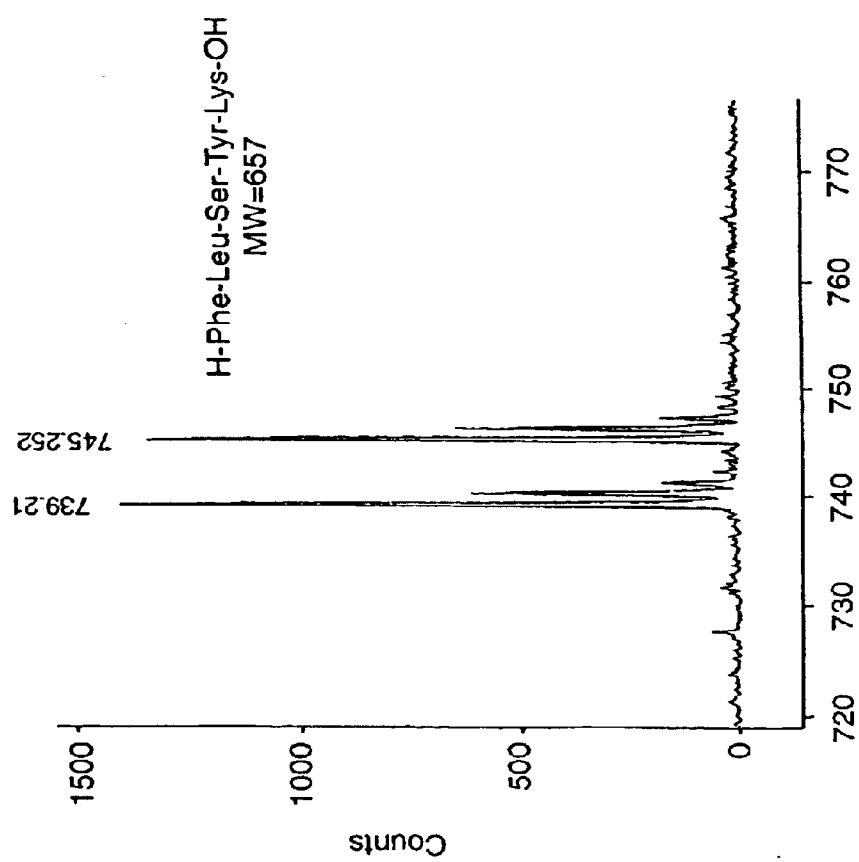

When analyzed by MALDI-MS in the positive ion mode, it is seen (FIG. 9) that a peptide with five amino groups (KNNQKSEPLIGRKKT; SEQ ID NO:1) can be quantitatively derivatized with this reaction. Internal standard peptides are acetylated with the trideuteroacetylated analogue of N-hydroxysuccinimide. This means that peptides in samples containing both the native and deuterated internal standard species (FLSYK; SEQ ID NO:2) would appear in the mass spectrum as a doublet (FIG. 10a). The presence of a carboxyl group in all tryptic peptides allows them to be analyzed by MALDI-TOF-MS in the negative ion mode. It was found that the $\epsilon$-amino group of all lysines can be derivatized in addition to the amino-terminus of the peptide, as expected. Arginine residues are not acetylated. This means that 3 amu would be added for each lysine when using trideutero-N-hydroxysuccinimide. The number of lysines in a peptide is revealed by the mass shift. (Multiple basic amino acids occasionally occur at the C-terminus with trypsin.) It is also possible to differentiate between peptides in which the only basic amino acid is lysine, or arginine, or a combination of the two. Peptides in which the only basic amino acid is lysine have no positive charge after acetylation. No spectra will be produced in the positive ion mode of ion acceleration unless a cationizing agent is added to the peptide. Actually, the peptide in this case picks up sodium and potassium ions from the matrix in the MALDI source, causing an increase in mass equivalent to that of sodium or potassium. Because the mass of these two ions is different, they appear in the spectrum as a double. When coupled with the fact that the lysine peptide described above in FIG. 10a is also deuterated, the mass spectrum of this peptide in the positive ion mode of acceleration will show four peaks (FIG. 10b).

Figures 11A, 11B:
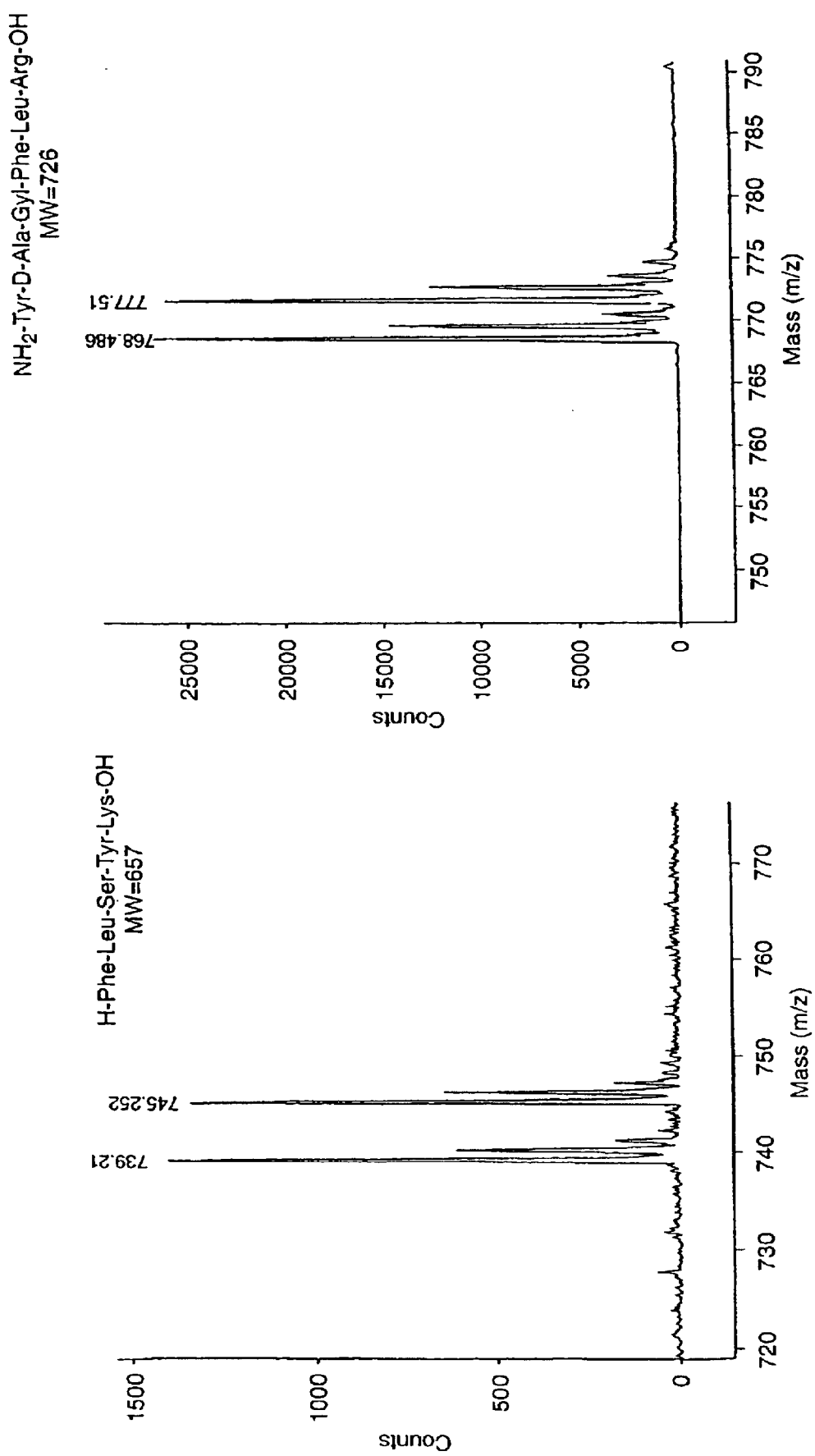
FIG. 11 is a MALDI mass spectrum of a peptide that contains (a) lysine and (b) arginine.

The mass spectrum for any peptide in a sample containing an isotopically labeled internal standard will appear as at least a doublet. The simplest case would be the one where (i) trideutero-NAS was used as the labeling agent, (ii) the C-terminus was arginine, and (iii) there were no other basic amino acids in the peptide. Spectra in this case show a doublet in which the two peaks are separated by 3 u (FIG. 11b). With one lysine the doublet peaks were separated by 6 u (FIG. 11a) and with two lysine by 9 u. For each lysine that is added the difference in mass between the experimental and control would increase an additional 3 u. Quantification of the relative amounts of both lysine and arginine containing peptides using MALDI-TOF and isotopically labeled internal standards was studied. A linear equation was deduced from the ion current intensity ratio of deuterium-labeled and unlabeled acetylated peptides versus the known ratio of the amount of these two peptides. The equation of the arginine-containing peptide (TAGFLR; SEQ ID NO:3) was $y=0.9509x-0.3148$ ($R^2=0.9846$) while that for a lysine-containing peptide (FLSYK; SEQ ID NO:2) was $y=0.9492x+0.4112$ ($R^2=0.9937$). The term y stands for the intensity ratio of the deuterium-labeled to unlabeled acetylated peptides and x stands for the relative amount of these two peptides.

These results strongly suggest that a method in which internal standard peptides are created by isotopic labeling and ratios of native to internal standard species quantified by MS will be useful in determining the relative concentration of signature peptides.

It is concluded that isotopically labeled internal standard analysis provides a useful method for the quantification of peptides. There is a strong possibility that when coupled with signature peptide derived from proteins, these combined methods will provide a powerful new method for the quantification of multiple proteins in complex mixtures.

Example VIII

Sample Protocol for Analysis of Protein Expression

The following protocol is one of many according to the invention that are useful for analyzing protein expression levels.

Step 1. Reduction of control and experimental samples containing several thousand proteins in robotic sample handling system.

Step 2. Alkylate sulfhydryl groups in experimental sample. If cysteine selection is desired the alkylating reagent is an affinity tagged maleimide. If the selection will be for another amino acid, the alkylating agent is iodoacetic acid or iodoacetamide.

Step 2'. Alkylate sulfhydryl groups in the control sample. If cysteine selection is desired, the alkylating reagent is a heavy isotope affinity tagged maleimide. If the selection will be for another amino acid, the alkylating agent is heavy isotope labeled iodoacetic acid or iodoacetamide. This allows proteins originating from the experimental sample to be distinguished from those originating from the control sample.

Step 3. The experimental and isotopically labeled control samples are combined.

Step 4. The proteins are separated by 2-D electrophoresis or 2-D chromatography. Reduction and alkylation may destroy tertiary and quaternary structure of the proteins. This would have a large impact on electrophoresis and chromatography, but the results could still be extrapolated to the native protein sample.

Step 5. Purified or partially purified proteins are subjected to proteolysis; generally with trypsin, but any proteolytic enzyme or combination of enzymes could be used. Enzymatic digest would either be done in a robotic system or with an immobilized enzyme column.

Step 6. Digested samples are transferred directly to the MALDI plates.

Example IX

Use of Fragment Ions to Distinguish Isobaric Peptides

A C-terminal arginine containing peptide ($NH_2$—H-L-G-L-A-R—OH; 1 mg) (SEQ ID NO:4) was dissolved in 1 ml of 0.1M phosphate buffer pH 7.5. This solution was then divided into two equal parts (500 ul each). One part was acetylated with N-($^1H_3$) acetoxysuccinimide and the other was with N-($^2H_3$) acetoxysuccinimide. Both parts were then mixed and purified on a C18-reversed phase column (RPC). Fractions from the RPC were collected and subjected to ESI-MS/MS. The singly charged precursor ion isotope cluster of m/z 708.50/711.50 [M+H] was isolated and subjected to collision-activated dissociation (CAD).

The tandem mass spectrum given by the CAD of singly charged differentially acetylated precursor ion isotope cluster of Ac-HLGLAR-OH (m/z 708.50/711.50) (SEQ ID NO:4) yields fragment ions listed in Table 1. Both N- and C-terminal fragment ions of type a, b and y are present in this spectrum. Complete $b_n$ or $y_n$ ion series are not seen in this spectrum. All prominent N-terminal fragment ions (a and b type) appeared as isotope clusters, separated by 3 amu. In contrast, all C-terminal (y-type) fragment ions are not seen as isotope clusters separated by 3 amu; rather they coincide, since these ions do not contain an acetyl group. Isotope ratios of all b-ions were determined by the peak heights of acetylated form divided by the peak heights of trideuteroacetylated form. For example relative abundance (peak height) of m/z 534.1 divided by the relative abundance of m/z 537.2 was used to get the ratio 1.07 of b5 ion (see Tables 1 and 2). Fragment ions y5-y2 confirms the N-terminal sequence of Ac—H-L-G-L (SEQ ID NO:5), whereas fragment ions b5-b2 confirms the C-terminal sequence of G-L-A-R—OH (SEQ ID NO:6).

It is evident that the isotope labeling ratios carry through from the precursor ion to the fragment ions. This differential labeling can be used to achieve relative quantification of peptides by tandem mass spectrometry in proteomics. This also permits multiple precursor ions having the same mass ("isobaric peptides") to be readily distinguished and quantified after CAD of the parent ion in this second mass spectrometry dimension.

TABLE 1

Fragment ions assignments

| m/z of $^1H_3$-acetylation | m/z of $^2H_3$-acetylation | Assignments | m/z of $^1H_3$-acetylation | m/z of $^2H_3$-acetylation | Assignments |
|---|---|---|---|---|---|
| 691.3 | 694.3 | M-$NH_3$ | 673.3 | 676.3 | M-$H_2O$-17 |
| 690.3 | 693.3 | M-$H_2O$ | 648.3 | 651.3 | M-$H_2O$—Ac |
| 552.2 | 555.1 | b5 + $H_2O$ | 529.4 | 529.4 | y5 |
| 534.1 | 537.2 | b5 | 512.2 | 512.2 | y5-$NH_3$ |
| 463.1 | 466.1 | b4 | 416.3 | 416.3 | y4 |
| 350.0 | 353.1 | b3 | 399.3 | 399.3 | y4-$NH_3$ |
| 292.9 | 296.0 | b2 | 359.3 | 359.3 | y3 |
| 435.1 | 438.1 | a4 | 246.3 | 246.3 | y2 |

TABLE 2

Statistical analysis of fragment ion ratios of differentially acetylated peptide $NH_2$-H-L-G-L-A-R-OH (SEQ ID NO:4)

| Fragment ions | Experimental ratio | Mean +/− SD | Expected ratio | % Error |
|---|---|---|---|---|
| M-$NH_3$ | 9.6/9.0 = 1.07 | | 1.0 | |
| M-$H_2O$ | 7.54/7.5 = 1.0 | | 1.0 | |
| M-$H_2O$-17 | 0.64/0.61 = 1.05 | | 1.0 | |
| M-$H_2O$—Ac | 7.97/7.61 = 1.05 | | 1.0 | |
| b5 + $H_2O$ | 2.4/2.3 = 1.04 | 1.08 ± ±0.060 | 1.0 | 8.0 |
| b5 | 8.5/7.97 = 1.07 | | 1.0 | |
| b4 | 8.68/8.1 = 1.07 | | 1.0 | |
| b3 | 4.6/4.1 = 1.12 | | 1.0 | |
| b2 | 1.44/1.2 = 1.20 | | 1.0 | |
| a4 | 2.65/2.29 = 1.16 | | 1.0 | |

The complete disclosures of all patents, patent applications including provisional patent applications, and publications, and electronically available material cited herein are incorporated by reference. The foregoing detailed description and examples have been provided for clarity of understanding only. No unnecessary limitations are to be understood therefrom. The invention is not limited to the exact details shown and described; many variations will be apparent to one skilled in the art and are intended to be included within the invention defined by the claims.

What is claimed is:

1. A method for analyzing differences in protein content among plural protein samples, the method comprising:
fragmenting at least a first protein sample and a second protein sample to produce a first peptide pool and a second peptide pool;
isotopically labeling at least a portion of the peptides in at least one of the pools so as to permit resolution of otherwise identical peptides in the first and second peptide pools by mass analysis;
contacting peptides from at least a portion of both of the peptide pools with a capture moiety to yield affinity-selected peptides comprising an affinity ligand, wherein the capture moiety selects for the affinity ligand; and
analyzing the affinity-selected peptides by mass spectrometry to determine one or more differences between the first and second samples.

2. The method of claim 1 wherein the labeling step comprises labeling at least one of the N-termini or the C-termini of the portion of the peptides.

3. The method of claim 2 wherein the labeling step comprises labeling both the N-termini and the C-termini of the portion of the peptides.

4. The method of claim 2 wherein the affinity ligand is an endogenous affinity ligand.

5. The method of claim 1 wherein the affinity ligand does not comprise the isotope label.

6. The method of claim 1 further comprising combining at least portions of the first and second pools after the labeling step but prior to the analyzing step.

7. The method of claim 1 wherein the affinity ligand is endogenous.

8. The method of claim 7 wherein the endogenous affinity ligand comprises an antigen.

9. The method of claim 8 wherein the affinity ligand comprises at least one antigen selected from the group consisting of a sugar, a lipid, a glycolipid and a peptide.

10. The method of claim 1 further comprising chemically coupling the affinity ligand to peptides.

11. The method of claim 1 further comprising reducing and alkylating the protein samples prior to the fragmenting step.

12. The method of claim 1 wherein the affinity-selected peptides comprise at least one low abundance amino acid selected from the group consisting of cysteine, tryptophan, histidine, methionine and tyrosine.

13. The method of claim 1 wherein the affinity-selected peptides comprise at least one phosphate group.

14. The method of claim 1 wherein the affinity-selected peptides comprise at least one oligosaccharide.

15. The method of claim 1 further comprising, prior to the analysis step, contacting the affinity-selected peptides with a second capture moiety to yield a subset of affinity-selected peptides comprising a second affinity ligand, wherein the capture moiety selects for the second affinity ligand.

16. The method of claim 15 wherein the second affinity ligand is an endogenous ligand.

17. The method of claim 16 wherein the first affinity ligand comprises the isotope label.

18. The method of claim 1 further comprising fractionating the affinity-selected peptides prior to analysis.

19. The method of claim 18 wherein the fractionation technique is selected from the group consisting of reversed phase chromatography, ion exchange chromatography, hydrophobic interaction chromatography, size exclusion chromatography, capillary gel electrophoresis, capillary zone electrophoresis and capillary electrochromatography, capillary isoelectric focusing, immobilized metal affinity chromatography and affinity electrophoresis.

20. The method of claim 1 further comprising fractionating the affinity-selected peptides subsequent to the contacting step to produce a second subset of peptides for mass spectrometric analysis.

21. The method of claim 1 wherein the mass spectrometric analysis is selected from the group consisting of matrix assisted laser desorption ionization (MALDI), electrospray ionization (ESI), fast atom bombardment (FAB), electron impact ionization, atmospheric pressure chemical ionization (APCI), time-of-flight (TOF), quadrapole, ion trap, magnetic sector, ion cyclotron resonance mass, or combinations thereof.

22. The method of claim 1 wherein the labeling step comprises labeling the first peptide pool with a first isotopic variant of a chemical moiety and the second peptide pool with a second isotopic variant of the chemical moiety to yield peptides in the first and second pools that are chemically equivalent but isotopically distinct; and wherein the analyzing step comprises analyzing the first sample and second samples by mass spectrometry; and comparing the mass spectrometry of the first and second samples.

23. The method of claim 22 wherein the analyzing step further comprises:

generating a first isotope ratio for the samples labeled with the first isotopic variant;

generating a second isotope ratio for the samples labeled with the second isotopic variant;

comparing the first isotope label ratio with the second isotope label ratio, wherein a difference between the first isotope label ratio with the second isotope label ratio is indicative of a difference in the relative concentration of the labeled peptides in the first and second sample.

24. The method of claim 23 wherein the first and second samples are combined prior to the analyzing step.

* * * * *

UNITED STATES PATENT AND TRADEMARK OFFICE
CERTIFICATE OF CORRECTION

PATENT NO. : 6,872,575 B2
APPLICATION NO. : 10/244784
DATED : March 29, 2005
INVENTOR(S) : Fred E. Regnier It is certified that error appears in the above-identified patent and that said Letters Patent is hereby corrected as shown below:

Title Page
Item #75 in the Inventor Name, delete "Fred B. Regnier" and insert
    -- Fred E. Regnier --

Item #56 in the References Cited, insert each of the following U.S. PATENT DOCUMENTS:
    -- 2002/0037532 A1    03/28/2002    Regnier et al. --
    -- 2003/0054570 A1    03/20/2003    Qui et al. --
    -- 2003/0186326 A1    10/02/2003    Regnier --

In the References Cited, insert each of the following FOREIGN PATENT DOCUMENTS:
    -- WO 02/46770 A2    06/13/2002    PCT --
    -- WO 03/027682 A2    04/03/2003    PCT --

In the References Cited, insert each of the following OTHER PUBLICATIONS:
    -- Chen et al. "Site-Specific Mass Tagging with Stable Isotopes in Proteins for Accurate and Efficient Protein Identification" *Anal. Chem* 2000;72:1134-1143. --

-- Ji, Junyan, "Isotope Coding for Qualitative and Quantitative Study of Peptides and Proteins – a Global Internal Standard Technology in Proteomics" Ph.D. Thesis, Purdue University (cover date December 2001). --

-- Regnier et al. "Multidimensional Separation Systems for the Analysis of Very Complex Peptide Mixtures". Retrieved from http://www.richrom.com/assets/CD23PDF/pl25.pdf; June 5, 2000. --

-- Regnier et al., "The next frontier in proteomics: recognizing and identifying proteins in regulatory flux,", Poster Abstract, HPLC '99 - 23rd International Symposium on High Performance Liquid Phase Separation and Related Techniques, May 30-June 4, Granada, Spain (May 31, 1999). --

-- Wang, Shihong, "Novel Approaches in Proteomics to the separation and Quantitation of Cellular Protein Expression" Ph.D. Thesis, Purdue University (cover date August 2001).

-- Zhang, et al. "Fractionation of isotopically labeled peptides in quantitative proteomics." *Analytical Chemistry* 2001;72(21):5142-5149. --

UNITED STATES PATENT AND TRADEMARK OFFICE
CERTIFICATE OF CORRECTION

PATENT NO. : 6,872,575 B2
APPLICATION NO. : 10/244784
DATED : March 29, 2005
INVENTOR(S) : Fred E. Regnier It is certified that error appears in the above-identified patent and that said Letters Patent is hereby corrected as shown below:

Title Page (Continued)

-- Zhang et al. "Minimizing Resolution of Isotopically Coded Peptides in Comparative Proteomics" *J. of Proteome Research* 2002;*1*:139-147. --

On page 2, delete "Baj et al." and insert -- Bai et al. --

Signed and Sealed this

Sixteenth Day of September, 2008

JON W. DUDAS
*Director of the United States Patent and Trademark Office*

SEQUENCE LISTING

```
<160> NUMBER OF SEQ ID NOS: 6

<210> SEQ ID NO 1
<211> LENGTH: 15
<212> TYPE: PRT
<213> ORGANISM: Artificial Sequence
<220> FEATURE:
<223> OTHER INFORMATION: peptide with five amino groups

<400> SEQUENCE: 1

Lys Asn Asn Gln Lys Ser Glu Pro Leu Ile Gly Arg Lys Lys Thr
1               5                   10                  15

<210> SEQ ID NO 2
<211> LENGTH: 5
<212> TYPE: PRT
<213> ORGANISM: Artificial Sequence
```

```
<220> FEATURE:
<223> OTHER INFORMATION: internal standard peptide

<400> SEQUENCE: 2

Phe Leu Ser Tyr Lys
1               5

<210> SEQ ID NO 3
<211> LENGTH: 6
<212> TYPE: PRT
<213> ORGANISM: Artificial Sequence
<220> FEATURE:
<223> OTHER INFORMATION: arginine-containing peptide

<400> SEQUENCE: 3

Thr Ala Gly Phe Leu Arg
1               5

<210> SEQ ID NO 4
<211> LENGTH: 6
<212> TYPE: PRT
<213> ORGANISM: Artificial Sequence
<220> FEATURE:
<223> OTHER INFORMATION: arginine-containing peptide
<220> FEATURE:
<221> NAME/KEY: MOD_RES
<222> LOCATION: (1)..(1)
<223> OTHER INFORMATION: optionally acetylated

<400> SEQUENCE: 4

His Leu Gly Leu Ala Arg
1               5

<210> SEQ ID NO 5
<211> LENGTH: 4
<212> TYPE: PRT
<213> ORGANISM: Artificial Sequence
<220> FEATURE:
<223> OTHER INFORMATION: N-terminal sequence
<220> FEATURE:
<221> NAME/KEY: MOD_RES
<222> LOCATION: (1)..(1)
<223> OTHER INFORMATION: Acetylation

<400> SEQUENCE: 5

His Leu Gly Leu
1

<210> SEQ ID NO 6
<211> LENGTH: 4
<212> TYPE: PRT
<213> ORGANISM: Artificial Sequence
<220> FEATURE:
<223> OTHER INFORMATION: C-terminal sequence

<400> SEQUENCE: 6

Gly Leu Ala Arg
1
```